(12) United States Patent
Hatscher et al.

(10) Patent No.: US 7,928,369 B2
(45) Date of Patent: Apr. 19, 2011

(54) DEVICE FOR THE ANALYSIS OF ISOTOPE RATIOS

(75) Inventors: Deike Hatscher, Syke (DE); Andreas Hilkert, Delmenhorst (DE); Hans-Jurgen Schluter, Bremen (DE); Alexander Duhr, Ganderkesee (DE); Michael Krummen, Bad Zwischenahn (DE); Johannes Schwieters, Ganderkesee (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 174 days.

(21) Appl. No.: 12/241,930

(22) Filed: Sep. 30, 2008

(65) Prior Publication Data

US 2009/0159795 A1 Jun. 25, 2009

Related U.S. Application Data

(62) Division of application No. 12/294,562, filed on Feb. 12, 2009.

(51) Int. Cl.
*G01N 30/10* (2006.01)
*G01N 33/00* (2006.01)
*G01N 1/22* (2006.01)
*H01J 49/00* (2006.01)

(52) U.S. Cl. .......... 250/288; 250/281; 250/428; 422/93; 73/23.35; 73/863.02

(58) Field of Classification Search .................. 250/288, 250/281, 428; 422/93; 73/23.35, 863.02
See application file for complete search history.

(56) References Cited

U.S. PATENT DOCUMENTS

| | | | | |
|---|---|---|---|---|
| 3,374,606 A | * | 3/1968 | Baddour | ............................ 95/85 |
| 4,035,168 A | * | 7/1977 | Jennings | ..................... 73/864.85 |
| 4,414,857 A | * | 11/1983 | Brazhnikov et al. | ........ 73/863.11 |
| 4,705,669 A | | 11/1987 | Tsuji et al. | |
| 4,916,313 A | * | 4/1990 | Hall et al. | ...................... 250/282 |
| 5,447,556 A | * | 9/1995 | Pleil et al. | .......................... 95/87 |
| 5,473,951 A | | 12/1995 | Tomlin | |

(Continued)

FOREIGN PATENT DOCUMENTS

DE 27 48 685 A1 5/1979

(Continued)

OTHER PUBLICATIONS

Fessenden Julianna E. et al. "Rapid 18O analysis of small water and Co2 samples using a continuous-flow isotope ratio mass spectrometer", vol. 16, No. 13 (Jul. 15, 2002); pp. 1257-1260—Wiley abstract-p. 1257, col. 2, paragraph 2, fig 1.

(Continued)

*Primary Examiner* — Nikita Wells
(74) *Attorney, Agent, or Firm* — Smith Gambrell & Russell LLP

(57) ABSTRACT

A method for the analysis of isotope ratios, wherein at least one sample gas and/or at least one reference gas are supplied to at least one analytical device via at least one open split, the addition of a carrier gas also being possible. According to the invention, the concentration of the sample gas and/or reference gas passing into the analytical device is controlled by the supply of the respective carrier gas or by direct supply of the sample gas into the analytical device. In the device according to the invention for supplying gases to at least one analytical device, two or more capillaries are provided for sample gases, the capillaries in each case having their own drive for the movement between mixing zone and waiting zone.

30 Claims, 13 Drawing Sheets

U.S. PATENT DOCUMENTS

2009/0314057 A1 * 12/2009 Hatscher et al. ............. 73/23.35

FOREIGN PATENT DOCUMENTS

| DE | 43 33 208 A1 | 6/1994 |
| DE | 44 21 272 A1 | 1/1996 |
| DE | 101 51 646 A1 | 6/2002 |
| EP | 0 306 333 A2 | 3/1989 |
| GB | 2 007 357 A | 5/1979 |
| WO | 2004/065956 A | 8/2004 |

OTHER PUBLICATIONS

Brooks P.C. et al. "Improved precision of coupled 13c and 15n measurements from sing samples . . . ", Rapid Communications in Mass Spectrometry vol. 17, No. 16 (Aug. 30, 2003), pp. 1924-1926.

Werner Roland A. et al. "ConFlo III-an interface for high precision 13C and 15N analysis with an extended dynamic range" Rapid Communications in Mass Spectrometry vol. 13, No. 13, (Jul. 15, 1999) pp. 1237-1241.

Rockman Thomas et al. "Gas chromatography/isotope-ratio mass spectrometry for high-precision . . . " Rapid Communications in Mass Spectrometry vol. 17, No. 16 (Aug. 30, 2003) pp. 1897-1908.

Hathcock L. et al. "A versatile interface modification for gc/ms on benchtop instruments", Journal of High Resolution Chromatography, Wiley VCH, Weinheim, DE, vol. 13, No. 9 (Sep. 1, 1990) pp. 6;56-658

Ligon W.V. et al., "Adjustable Open-Split Interface for Gas Chromatography/Mass Spectrometry Providing Solvent Diversion . . . " Analytical Chemistry, American Chemical Society, Columbia, US, vol. 63, No. 20 (Oct. 15, 1991) pp. 2386-2390.

International Search Report.

European Search Report issued on corresponding European Divisional Application No. 09 00 7745 (Jul. 29, 2009).

* cited by examiner

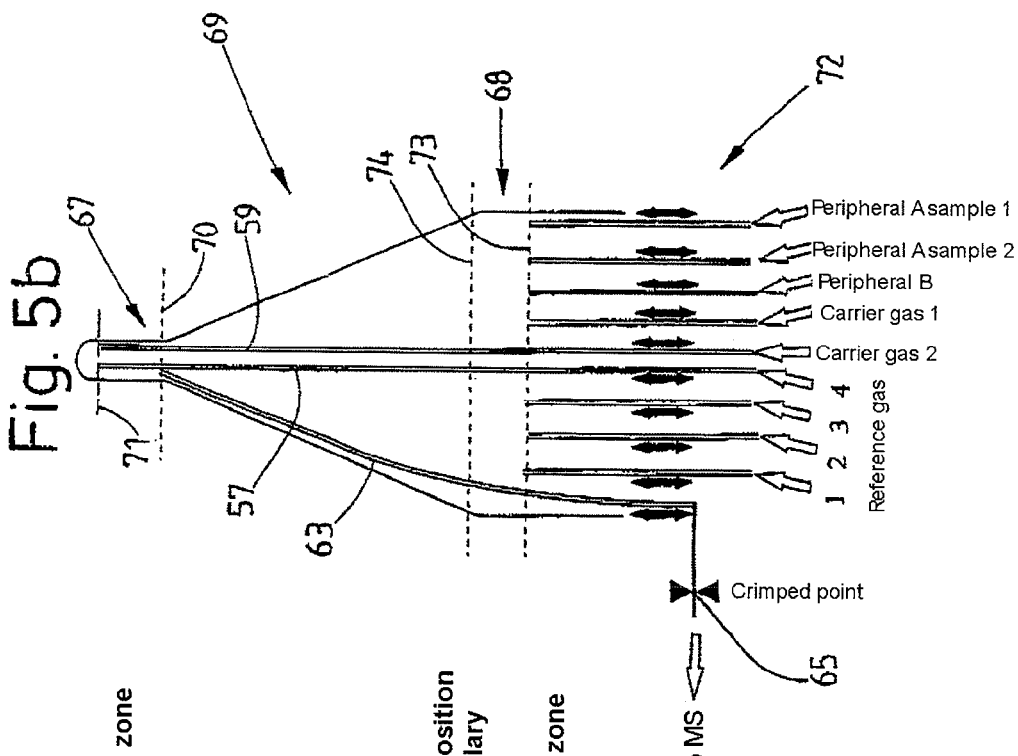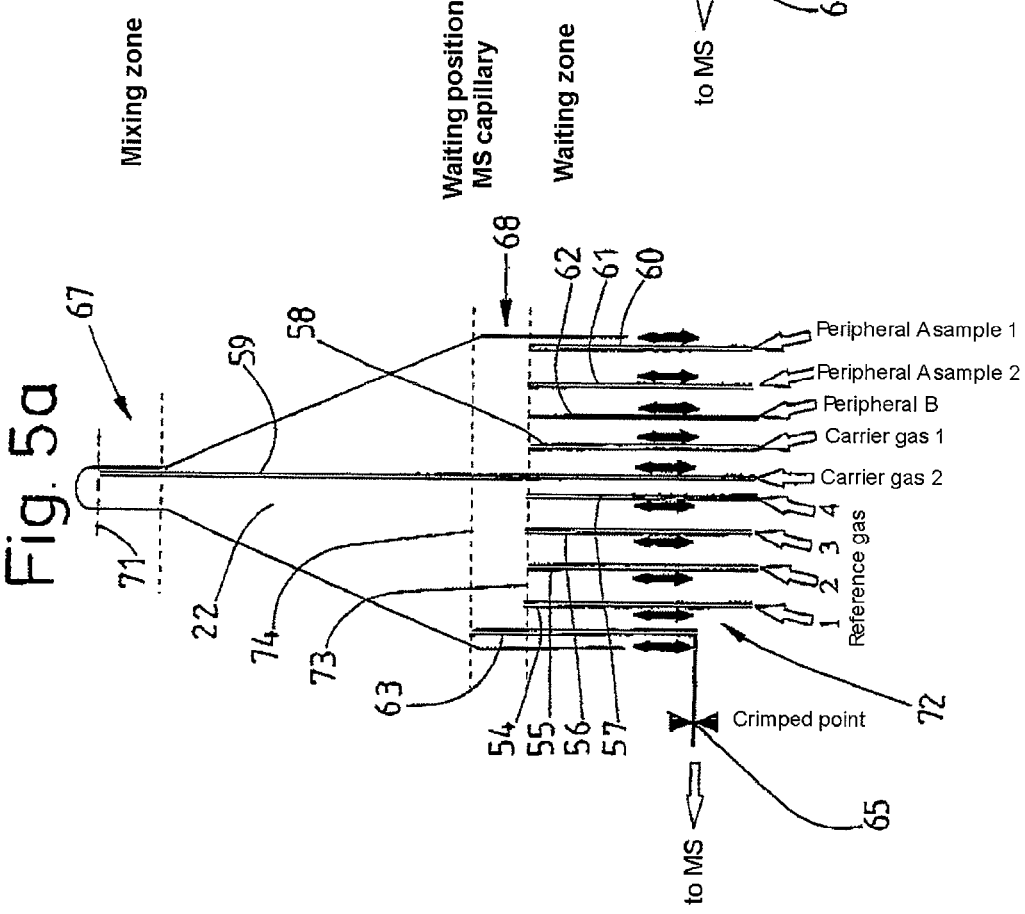

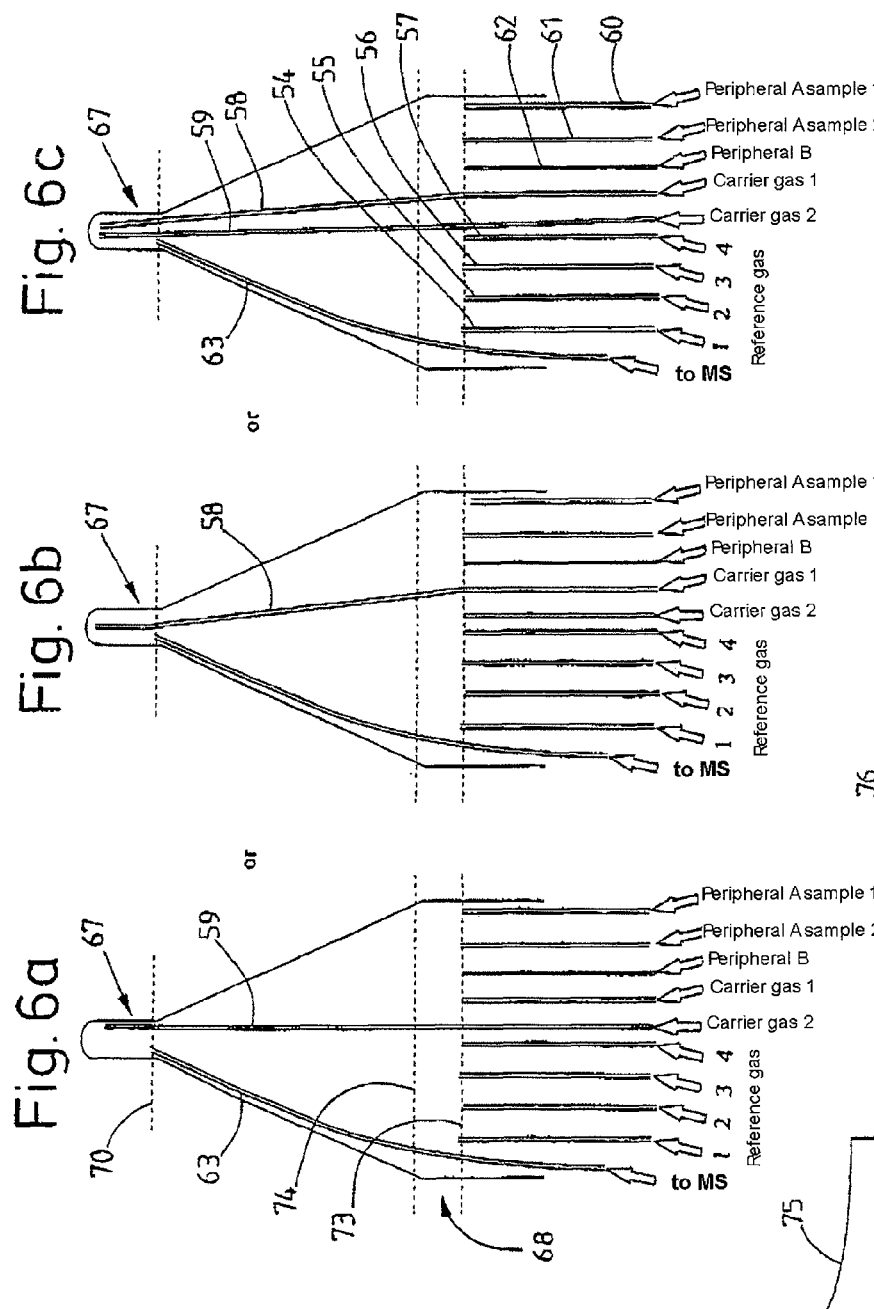

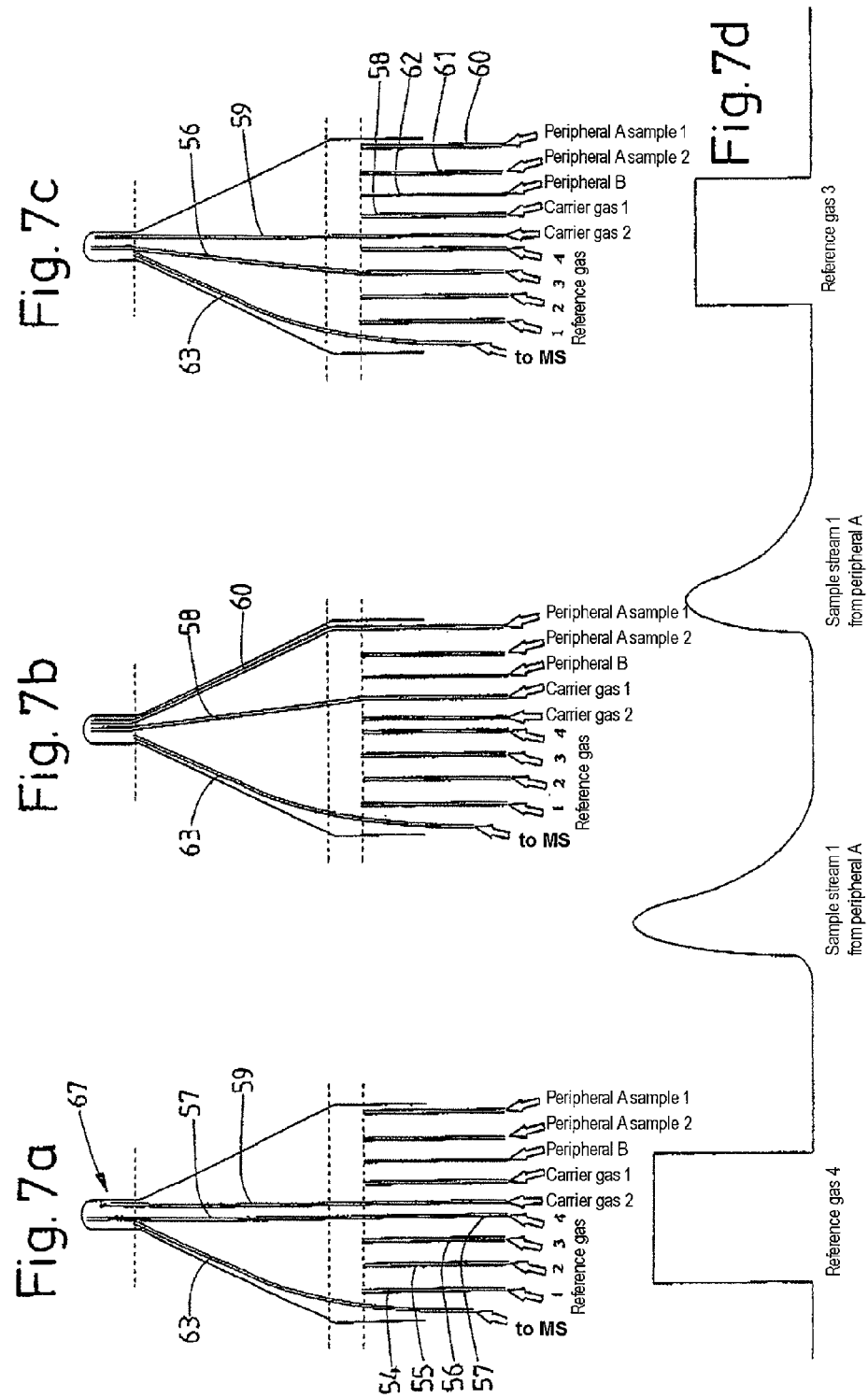

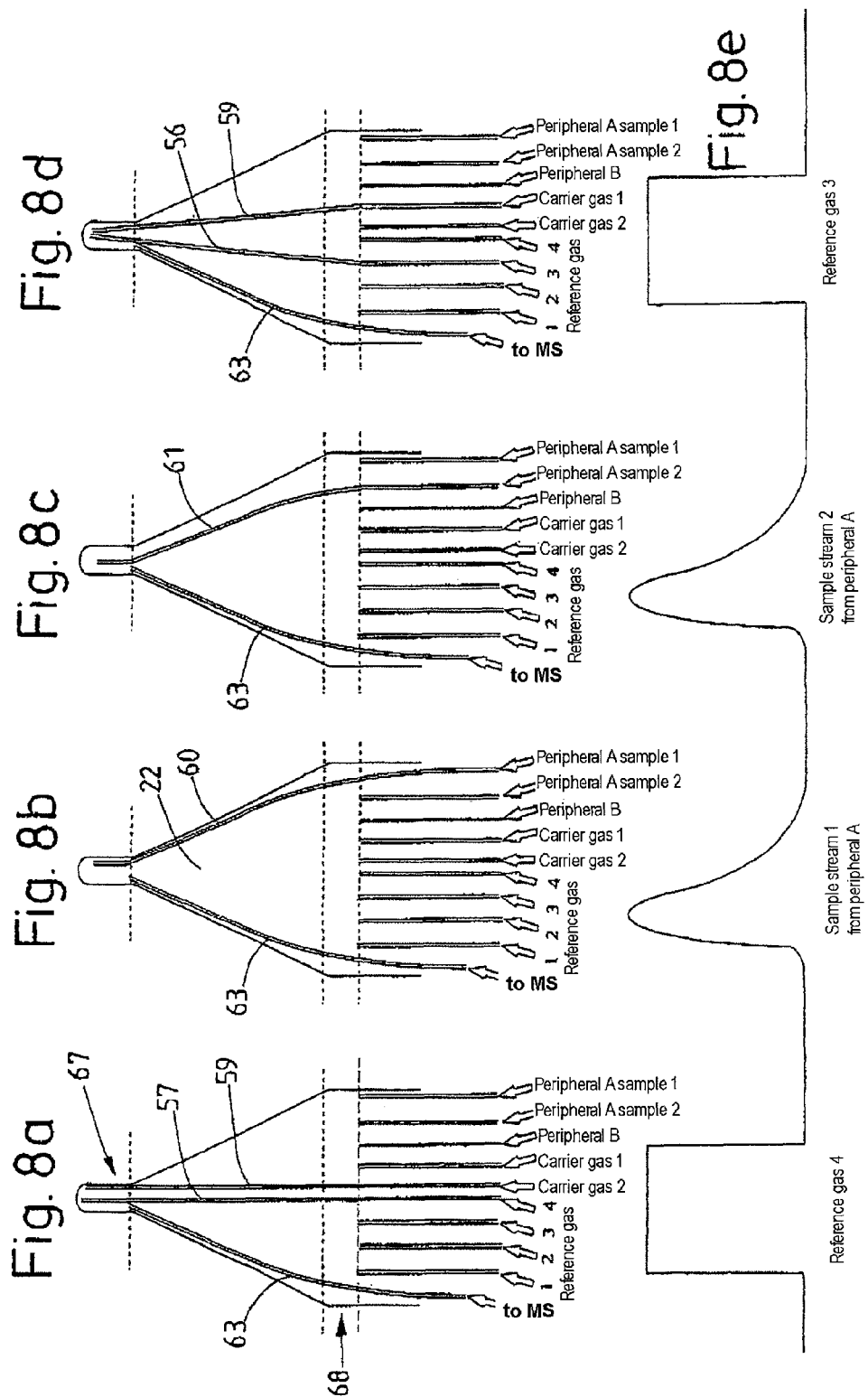

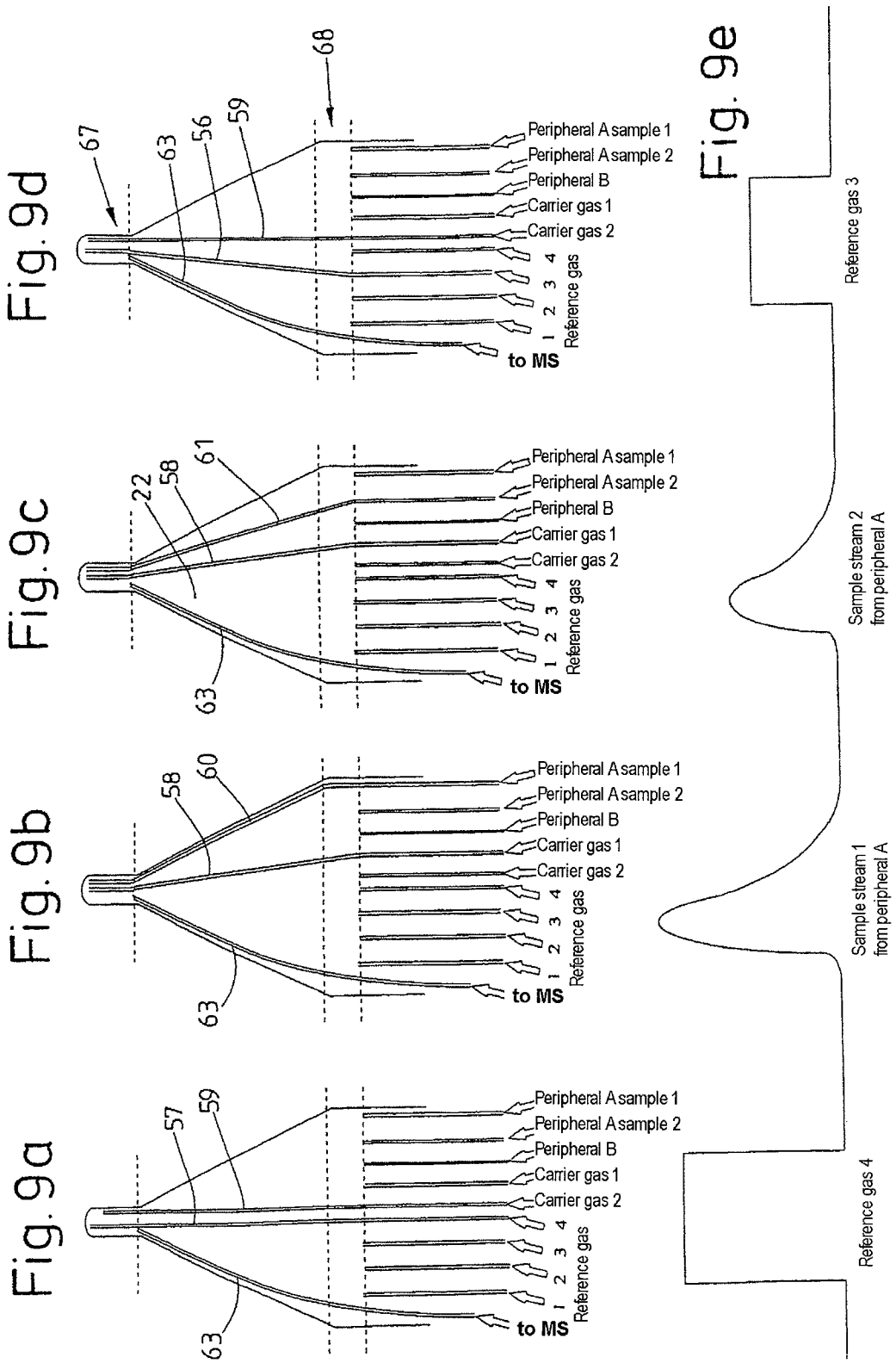

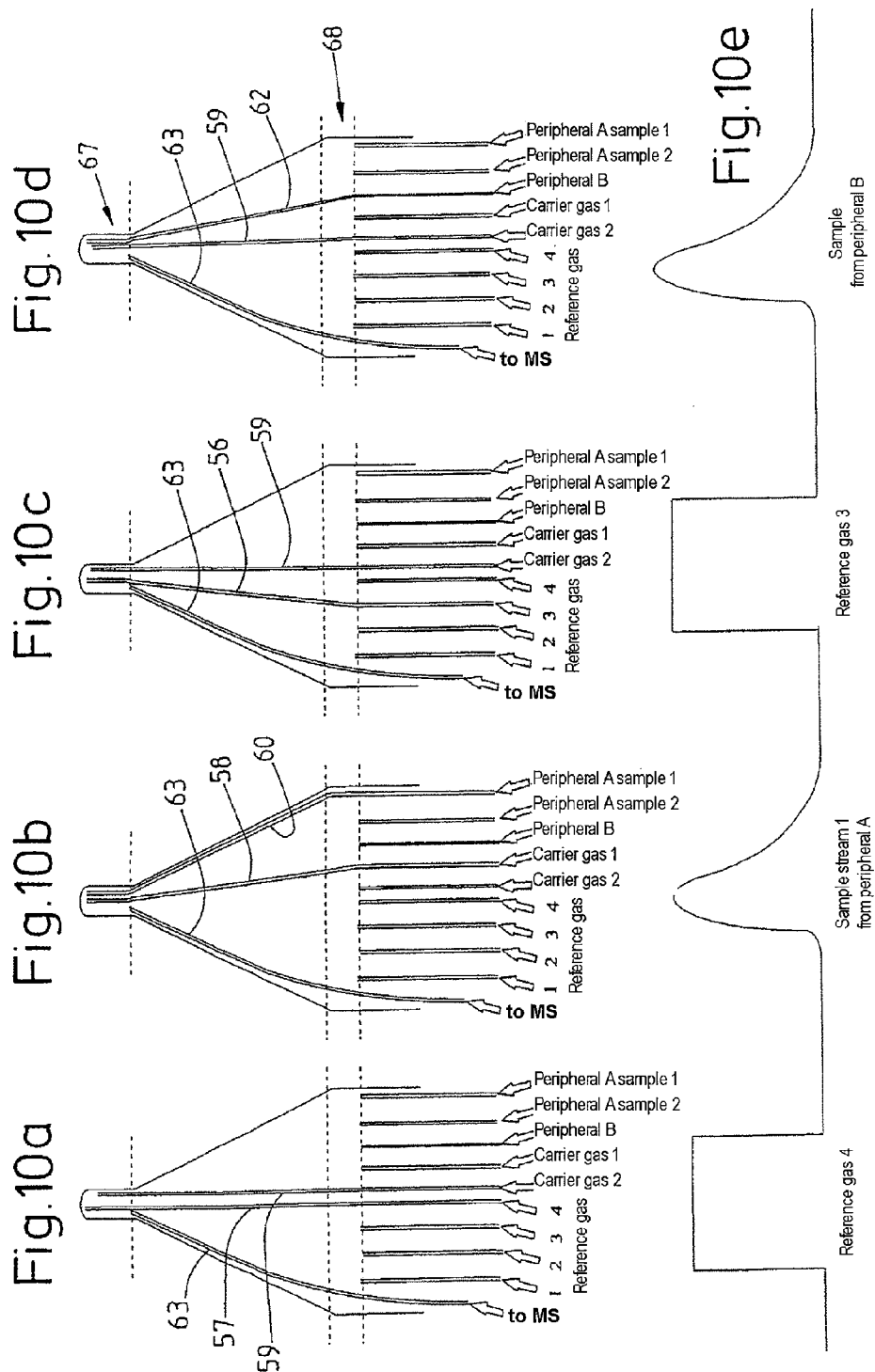

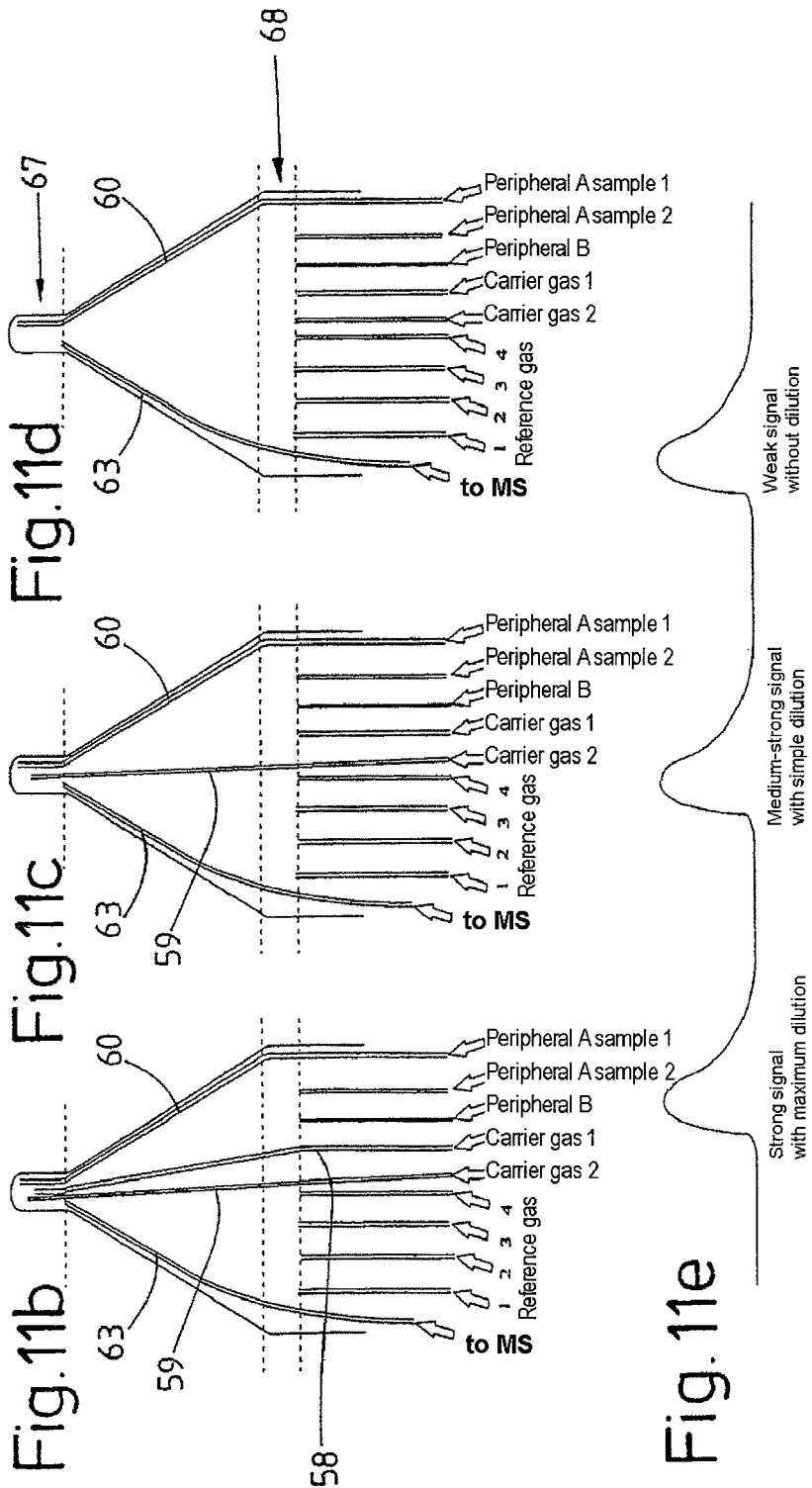

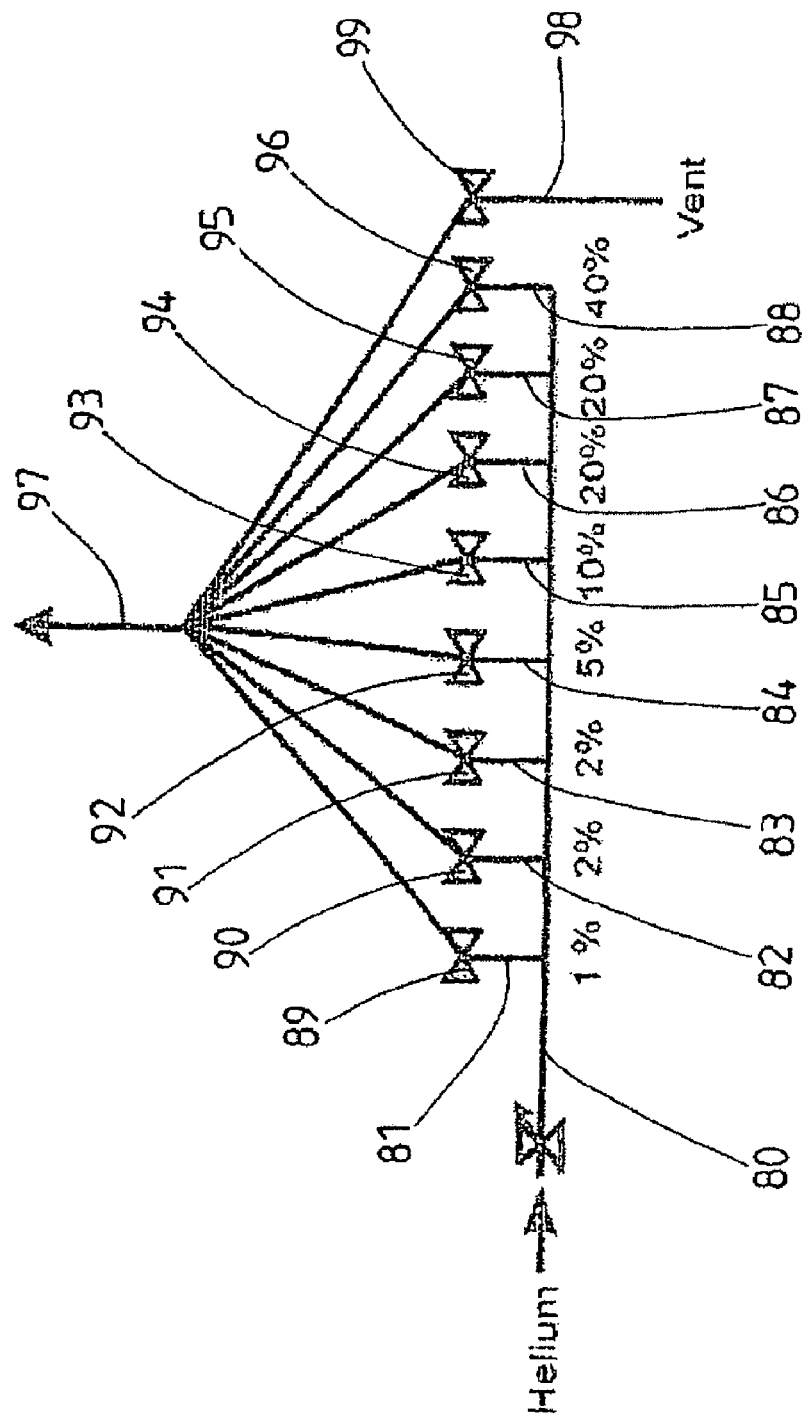

DEVICE FOR THE ANALYSIS OF ISOTOPE RATIOS

STATEMENT OF RELATED APPLICATIONS

This application is a divisional application deriving from U.S. patent application Ser. No. 12/294,562 having a filing date of Feb 12, 2009, which is based on PCT International Application No. PCT/EP2007/002642 having an International Filing Date of 26 Mar. 2007, which claims priority on German Patent Application No. 10 2006 015 535.1 having a filing date of 31 Mar. 2006.

BACKGROUND OF THE INVENTION

1. Technical Field

The invention relates to a method for the analysis of isotope ratios, wherein at least one sample gas and/or at least one reference gas are supplied to at least one analytical device via at least one open split, the addition of a carrier gas also being possible. In addition, the invention relates to a device for supplying gases to at least one analytical device, particularly for carrying out the said method, comprising an open split which has a mixing zone and a waiting zone, wherein, in the waiting zone, capillaries for sample gas, carrier gas and/or reference gas and a capillary for removing the gases, particularly for supplying the gases to the analytical device, are arranged, wherein the capillaries can be moved into the mixing zone or to the mixing zone and back again.

2. Related Art

A special feature of devices for determining isotope ratios is that all components must be constructed in such a manner that no fractionations occur. These can occur, for example, wherever there is transport by diffusion.

An open split as interface between a mass spectrometer suitable for the analysis of isotope ratios (isotope mass spectrometer or IRMS) and a gas chromatography device is described, for example, in DE 43 33 208 A1. The analysis of $CO_2$ and $N_2$ when using helium as carrier gas is mentioned there. The quantity of the carrier gas supplied is variable so that the dilution of the two gases to be analyzed can be matched to one another. The volume of carrier gas is changed via suitable valves or by changing the position of capillaries immersed into the open split. To be able to correctly adjust the various gas streams and quantities in the sense of the results aimed for, the operating personnel requires great experience. The results of the analysis depend on the skill of the operating persons and fluctuate more or less randomly.

BRIEF SUMMARY OF THE INVENTION

It is the object of the present invention to improve the method for the analysis of isotope ratios, mentioned initially. In particular, the analysis results should reflect the actual ratios even more accurately.

The method according to the invention is characterized by the fact that the concentration of the sample gas and/or reference gas passing into the analytical device is controlled by the supply of the respective carrier gas or by the direct supply of the sample gas into the analytical device. A computer-controlled control system is preferably provided, particularly with the possibility for feedback by means of sensor data and/or the repetition of parameters already used earlier. The term "control" must here be interpreted widely in principle and should include an adjustment or control without feedback and a control in the narrower sense with feedback (as in automation technology). The control can be implemented by software or hardware. It is preferably a program-controlled control. At least actuators, known as such, for the carrier gas, for example electronically controllable valves and/or actuators for capillaries entering into the open split, are controlled. The control also includes the possibility of controlling the carrier gas supply down to zero. In addition, sample gases and reference gases can contain carrier gas even before they enter into the open split (premixed gases).

As an analytical device, a mass spectrometer, particularly a mass spectrometer suitable for isotope ratio measurement (IRMS) is preferably provided. However, the invention is not restricted to this. Other for example optical analyzers, spectrometers, interferometers, spectral analyzers etc. can also be used.

An advantageous development of the invention provides that the open split has capillaries with different effective flow rates for at least one of the gases—sample gas, carrier gas, reference gas—and that the gas stream is controlled by selection and activation of the capillaries with the desired flow rate. In addition or as an alternative, it can be provided that the gas streams are also controlled in another manner, for example by controllable valves. The possibility then exists that at least a coarse control is effected by means of the selection of a particular capillary and additionally a fine control is effected by a corresponding actuator. The different effective flow rates of the individual capillaries can result, for example, from different cross sections or lengths of the capillaries or from defined cross sectional constrictions, for instance at end pieces of the capillaries. For each gas, several capillaries can also be provided.

Advantageously, only the inflow of the respective carrier gas is controlled whilst the remaining gas streams remain uncontrolled. This measure simplifies the equipment construction and the circuit or program complexity within the control system.

The carrier gas supply is advantageously changed in steps, wherein mutually parallel carrier gas part-streams of equal or different amplitude can also be activated and combined with one another for adjusting a resultant carrier gas stream.

The inflow of the respective carrier gas is advantageously controlled in such a manner that the concentration of the sample gas and/or reference gas remains essentially constant, at least within a measuring range which is optimum for the analytical device. The volume flow of the sample gas fluctuates in dependence on the source used. For example, the supply of gas from a gas chromatograph or an element analyzer is known. In this context, the sample volume in the gas stream streaming into the open split through the sample capillaries is subject to fluctuations. These can be compensated for by a corresponding inflow of carrier gas so that the sample gas always reaches a concentration which is optimum for the analytical device. This analogously applies to the reference gas.

For many applications, particularly for the correct dilution of the reference gases, it is appropriate to record the relation between dilution control and analyzer signal in advance and then to directly use the previously calibrated adjustments in the course of the measurement. This is particularly efficient in connection with the incremental flow control according to the invention, discussed further below. Thus, a correction during the actual measuring process can be completely eliminated.

An advantageous development of the invention provides that the inflow of the respective carrier gas during a continuous alternating measurement is controlled in such a manner that sample gas and reference gas supply signals of essentially equal intensity in the analyzer. Usually, sample gas and reference gas are supplied alternatingly with carrier gas to the analyzer. To reduce measuring inaccuracies, the carrier gas inflow during the sample gas measurement and/or the reference gas measurement is controlled in such a manner that, if possible, the same signal strength arrives in the analyzer. When a mass spectrometer is used, this means a supply of carrier gas such that sample gas and reference gas produce almost the same number of hits per unit time at the detector of the mass spectrometer. In this arrangement, a feedback of the intensity can be provided in order thus to control the inflow of the carrier gas.

The concentration of the sample gas is advantageously derived from the measurement performed by the analyzer and the result of the measurement is used for controlling the inflow of the respective carrier gas. In this embodiment, the measurement result of the analyzer is included in the control loop. On the basis of this, the inflow of the carrier gas can be controlled for the sample gas and/or the reference gas even for subsequent measurements.

The concentration of the sample gas is advantageously derived from a concentration measurement before entry of the sample gas into the analyzer, particularly before entry into the open split, and the result of the measurement is used for controlling the inflow of the carrier gas. This is an alternative or supplement for the control system mentioned immediately before.

In a development of the invention, it can be provided that the concentration of the sample gas is derived from the thermal conductivity. Detectors suitable for this purpose are known and can be included relatively simply into the control loop for the inflow control of the carrier gas.

The open split advantageously operates in accordance with the direct-current principle. This facilitates the equipment construction in carrying out the method and the management of the flow parameters.

According to a further concept of the invention, the open split can be supplied with two or more sample gases, the inflow of the carrier gas being controlled for each sample gas. In this manner, the measurements of different sample gases can also be compared with one another. Providing and setting up a number of open splits can thus be avoided.

As a development of the invention, it can be provided that the sample gas, before entry into the open split, is divided into two or more part-gas streams which are supplied to the open split. The sample gas is advantageously distributed over two or more capillaries which enter the open split in parallel with one another. The part-gas streams in the various capillaries can thus be influenced in different ways, for example chemically or physically changed, before entry into the open split. The use of different capillaries is also possible.

At least one of the part-gas streams, before entry into the open split, is advantageously conducted through a trap so that a component or substance contained in this part-gas stream is held back at least partially. For example, a sample gas which jointly contains $CO_2$ and $N_2$ can be conducted through an ascarite trap which traps the $CO_2$ which disturbs the $N_2$ measurement. $CO_2$ has the unpleasant characteristic of disturbing also subsequent $N_2$ measurements by a long time. The method according to the invention enables a part-gas stream to be generated which, in this case, is free of $CO_2$ and allows a high-quality measurement of $N_2$.

To gain time between two chromatographic peaks—for example for a measurement of the suitable reference gas—a delay loop, for example in the form of a suitably long capillary, can be added if necessary.

The method is provided for the analysis of the isotope ratios of light- and medium-weight elements. Sample gas are particular compounds of these elements which can be changed into the gas phase, e.g.: $H_2$, $CO_2$, CO, $N_2$, $SO_2$, $N_2O$, NO, $SF_6$, $SF_3$, SO, $Cl_2$, noble gases. Compounds of H, C, N, O, S, Cl, particularly $H_2$, $CO_2$, CO, $N_2$, are preferred.

According to a further concept of the invention, it is provided that the sample gas and the reference gas are supplied to the analytical device via different open splits and with or without carrier gas. In this alternative, accordingly, the sample gas is supplied via a different open split than the reference gas. Both open splits can be supplied with carrier gas for mixing and dilution.

The supply of carrier gas into at least one of the two open splits is advantageously controlled by dividing the carrier gas stream into several parallel part-gas streams, of which one or more are selected and supplied to the open split. The part-gas streams can reach the open split in parallel next to one another or can first be combined to form a single carrier gas stream entering the open split. By blocking or letting pass the individual part-gas streams, a resultant carrier gas stream with the desired flow rate can be adjusted.

Some or all parallel part-gas streams are preferably of different magnitude. This provides a particularly large number of variations when adjusting the resultant carrier gas stream.

According to another concept of the invention, the sample gas, before being supplied into the open split, is divided into a stream leading to the open split and a stream, separated therefrom, which is not supplied to the open split. In this manner, too high a sample gas stream can be reduced to a lesser flow rate so that only the desired sample gas stream arrives in the open split.

The device according to the invention is characterized by the fact that two or more capillaries are provided for sample gases and that the capillaries in each case have their own drive for the movement between mixing zone and waiting zone. Using the device, several samples can thus be supplied at the same time and/or under the same equipment conditions to one or more analyzers or analytical devices. The calibrations normally used before carrying out measurements can thus be considerably simplified since, in the best case, only an open split is now used. Preferably, several capillaries are provided both for reference gases and sample gases in the open split, possibly also several capillaries for different carrier gases.

The drives for the capillaries are advantageously actuators. In this arrangement, the drives for the capillaries can be driven by a common central control unit so that the capillaries can be displaced with computer assistance and only the capillaries needed are in the mixing zone whilst the capillaries not needed are parked in the waiting zone.

According to a further concept of the invention, the waiting zone has a larger cross section than the mixing zone. The larger cross section of the waiting zone is advantageous for accommodating the many capillaries. The smaller cross section of the mixing zone shortens the dead times in the case of overflows and mixing of the gases since, with the smaller cross section of the mixing zone, its volume is also distinctly reduced.

The cross section of the waiting zone is advantageously at least twice as large as the cross section of the mixing zone, preferably at least five times as large. Depending on the number of capillaries and space required by them, the ratio of cross sections can also be distinctly greater.

According to a further concept of the invention, the open split has, between the mixing zone and the waiting zone, a funnel-shaped area with an essentially conical shape and a cross section decreasing towards the mixing zone. Due to the shape described, the capillaries can be displaced without problems between the waiting zone and the mixing zone. The capillaries are preferably elastically bendable and can follow the course of the wall in the funnel-shaped area.

The length of the mixing zone (in the direction of the capillaries) is advantageously greater than the width of the mixing zone, particularly by a factor of two to three. Other relations are possible. It is important that the volume of the mixing zone is limited. In addition, different positions of the capillaries should be possible within the mixing zone.

In a development of the invention, it can be provided that a waiting position of the capillaries for the removal of the gases—within the waiting zone—is closer to the mixing zone than waiting positions of the remaining capillaries. The capillary for the removal of the gases, for example, leads to an isotope mass spectrometer or another analyzer for examining isotope ratios. The described waiting position of the capillaries for the removal of the gases ensures that no substances from the remaining capillaries located in the waiting zone reach this capillary.

It is advantageously provided that a removal position of the capillaries for the removal of the gases—within the mixing zone—is closer to the waiting zone than the mixing positions of the remaining capillaries. The result is that the mixing of the gas concerned, for instance a sample gas with a carrier gas, can take place in the best possible manner before the gases enter into the capillaries for the removal of the gases.

According to a further concept of the invention, it can be provided that the capillary for removing the gases is connected to a line which has a crimped point. The crimped point accurately defines the smallest cross section of the line significantly influencing the volume flow.

The capillary for removing the gases is advantageously connected to a line which consists of inertized high-grade steel. As a result, reactions in the widest sense (chemical reactions, background effects etc.) of the line with the gases flowing through can be avoided. This particularly applies in conjunction with the gases normally analyzed in isotope ratio measurements.

As a development of the invention, it can be provided that the open split is arranged inside an analyzer, particularly inside an isotope mass spectrometer. In conventional measuring devices, an analyzer is coupled to one or more peripherals. For this purpose, the analyzer has a corresponding interface, for example connections for one or more open splits. In the known devices, the open splits are thus located outside the analyzer. This means that the open splits are exposed to the conditions prevailing outside the analyzer, for example changing temperatures (also in internal spaces). With the arrangement according to the invention, the existing open splits are provided within the analyzer so that the ambient conditions relevant also to the accuracy of the measurements can be kept controlled or constant, respectively. In concrete terms, the analyzer can have a housing in which one or more open splits are arranged. At the housing or conducted out of it there are interfaces, connected to the open split, for the connection of sample gases, carrier gases and reference gases. The interfaces can be line couplings, known in principle, which are combined with valves. The valves are preferably controllable individually and particularly under computer control. A central control unit carries out the automatic electronic inflow control explained initially.

The open split is advantageously constructed in accordance with the direct-current principle, namely with gases streaming in exclusively from one and the same direction and particularly with a mixing zone closed on one side. When relatively light carrier gases are used, the waiting zone is then arranged below the mixing zone whilst a reverse arrangement is used for relatively heavy carrier gases.

According to a further concept of the invention, it can be provided that capillaries with different effective flow rates are provided at least for one of the gases—sample gas, carrier gas, reference gas. The different flow rates can be achieved, for example, by capillaries having different cross sections, defined cross sectional constrictions, different lengths etc. By selecting or activating the corresponding capillaries, a gas having the desired flow rate can be selectively supplied to the open split. The flow rates can be finely adjusted additionally or alternatively via electronically driven valves.

The subject matter of the invention is also a device for supplying gases to an analytical device, wherein a particular gas stream can be adjusted in a gas line, with a feed line and at least one ongoing line and several valves between the feed line and the ongoing line, wherein the valves are connected in parallel with one another and can be switched step by step—binary or incrementally. The gas stream in the gas line is accordingly not adjusted by more or less strong actuation of a single valve. Instead, it is assumed that a valve can only adopt a few, preferably two, discrete switching states. An open valve allows a certain gas stream to pass, two open valves allow a gas stream about twice as high etc. A stepped opening of the valves is also conceivable, for example with the adjustments closed/quarter open/half open/completely open.

A defined restriction having a corresponding flow rate is advantageously allocated to each valve. Via the restriction, the gas stream is defined when the respective valve is completely open. The restriction is either provided additionally to the valve or integrated in the valve.

The restrictions of at least two valves advantageously differ. As a result, the most varied gas stream values can be adjusted with a few parallel valves.

Advantageously, several restrictions are provided, the flow rates of which differ by the same factor. For example, a factor of 2 or 2.5 can be provided. Without specifying dimensions, the flow rates 1/2/4/8 . . . or 1/2.5/6.25/15.625 etc. are then obtained. Other factors can also be represented.

The valves can be controlled advantageously manually, electrically or electronically. The valves can also be part of a control loop. In the simplest embodiment, the valves are manually preset.

Advantageously, a parallel line without valve is additionally provided for the connection of feed line and ongoing line. The parallel line extends in parallel with the valves and ensures that a defined gas stream always flows. This gas stream advantageously meets the minimum flow requirements of the associated open split.

According to a further concept of the invention, the device is characterized by an open split, following the ongoing line, for mixing the gas stream with another gas stream. The gas stream passing into the open split is then adjusted via the valves.

According to the invention, a second ongoing line can also be provided, several valves also being arranged in parallel with one another between the second ongoing line and the feed line. Accordingly, the feed line feeds two ongoing lines, these in each case having a separate group of valves for adjusting the respective gas stream.

Advantageously, defined restrictions having corresponding flow rates are also in each case allocated to the valves for the second ongoing line.

According to a further concept of the invention, a separate open split, namely a second open split is allocated to the second ongoing line. In consequence, the gas stream can be divided over two different open splits.

A mass spectrometer advantageously follows the open split or the two open splits as analyzer. In particular, this is an isotope mass spectrometer, a mass spectrometer with plasma source (ICP-MS), a mass spectrometer with collision-gas control for collision and reaction cells. Using the device according to the invention, the carrier gas stream or a collision-gas stream to the analyzer or to the analytical device is advantageously adjusted or controlled.

According to the invention, the feed line can have a branch to bypass the valves and for the direct supply into the open split. The branch does not have any, or has only a relatively weak, restriction so that a gas stream is possible here which is greater than or equal to the gas stream through the otherwise most severe restriction.

According to a further concept of the invention, it is provided that the open split or one of the open splits has a first capillary for supplying gas with a high flow rate and a second capillary for supplying gas with a comparatively lower flow rate. Preferably, sample gas of different concentration is supplied via the first and second capillary whilst carrier gas passes into the open split via the ongoing line with a subsequent capillary.

According to the invention, the open split can have a capillary for removing gas—snifting capillary—which is arranged in the direct current relative to the first or second capillary and which is arranged in the countercurrent to the respective other capillary—second or first capillary. The second capillary for supplying gas with a low flow rate is preferably arranged in the countercurrent to the snifting capillary. Correspondingly, the first capillary, namely the capillary for supplying gas with a high flow rate, is then arranged in the direct current to the snifting capillary.

According to a further concept of the invention, the snifting capillary has an outside diameter which is smaller than the inside diameter of the second capillary for supplying gas. In addition, snifting capillary and second capillary are arranged movably relative to one another and coaxially with respect to one another, in such a manner that, in one position, the snifting capillary dips into the second capillary and, in another position, the two capillaries have a distance from one another.

According to a further concept of the invention, the open split or one of the open splits has a capillary for supplying gas. In this arrangement, this capillary has a branch which can be closed via a valve. The valve here preferably has the function of reducing the gas stream or the flow rate through the capillary. When the valve is open, a part-gas stream flows out of the branch so that only a corresponding part-gas stream reaches the open split via the capillary.

According to a further concept of the invention, the open split or one of the open splits has a capillary for supplying gas, two or more feed lines opening into this capillary. In this manner, different gases or gas samples can be conducted into a capillary.

According to the invention, it can be provided that the feed lines have multi-path valves which, let the gas pass in the direction of the open split in one switch position and divert the gas in another switch position. These are preferably three-way valves. They conduct the gas either in the direction of the open split or in the direction of another target. This provides for constant pressure conditions in an area preceding the feed lines, a so-called peripheral.

According to a further concept of the invention, carrier gas can be supplied into two different open splits via the feed line, wherein sample gas can be supplied into one of the open splits via a capillary, wherein reference gas can be supplied into the other open split via a capillary, and wherein, from both open splits, snifting capillaries lead to an analyzer.

The subject matter of the invention is also a device for supplying sample gas and carrier gas to an analytical device, having the following features:
a) a first capillary for carrier gas leads into an open split,
b) a second capillary for sample gas having a low flow rate leads into the open split,
c) a third capillary for sample gas having a comparatively higher flow rate leads into the open split,
d) a fourth capillary leads as snifting line from the open split to the analytical device.

Accordingly, so-called low-flow sample gas, on the one hand, and high-flow sample gas, on the other hand, pass via the same open split into the analytical device.

The first capillary is preferably preceded by a carrier gas feed line with branch, the branch being connected to the second capillary for the sample gas of low flow rate. In the branch, a valve can be provided which blocks or lets pass the gas stream in the branch.

The fourth capillary, as snifting line, can advantageously dip into the second capillary for the sample gas with a low flow rate. The sample gas with a low flow rate is thus passed directly to the snifting capillary.

BRIEF DESCRIPTION OF THE DRAWINGS

Further features of the invention are obtained from the claims and from the description in the remainder. Advantageous exemplary embodiments of the invention will be explained in greater detail in the text which follows, with reference to drawings, in which:

FIGS. 5a, 5b show an open split in two different configurations, namely, on the one hand, in an off configuration and, on the other hand, during the transmission of carrier-gas-diluted reference gas into the mass spectrometer.

FIGS. 6a, 6b, 6c, 6d show the open split as shown in FIGS. 5a, 5b, in this case with three different configurations, namely with an activated one of two possible carrier gas capillaries or with both activated carrier gas capillaries so that a mixing zone is freed of possibly existing strongly absorptive gases in order to subsequently be able to carry out experiments with less background.

FIGS. 7a, 7b, 7c, 7d show three configurations of the open split according to FIGS. 5a, 5b, in this case together with the representation of the signal intensities for two reference gas pulses and two sample gas pulses.

FIGS. 8a-8e show four different configurations of the open split, in this case together with the representation of the signal intensities of two reference gas pulses and two sample gas pulses.

FIGS. 9a-9e show four configurations of the open split, in this case with the representation of the signal intensities of two reference gas pulses and two sample gas pulses.

FIGS. 10a-10e show four configurations of the open split, in this case with the representation of the signal intensities of two reference gas pulses and two sample gas pulses.

FIGS. 11a-11e show three configurations of the open split according to FIG. 5, in this case with the representation of the signal intensities of the sample gas, on the one hand with uniform dilution and, on the other hand, with changing dilution.

FIG. 12 shows a diagrammatic representation of the control of a gas stream by means of mutually parallel valves.

DETAILED DESCRIPTION OF PREFERRED EMBODIMENTS

Figure 1:
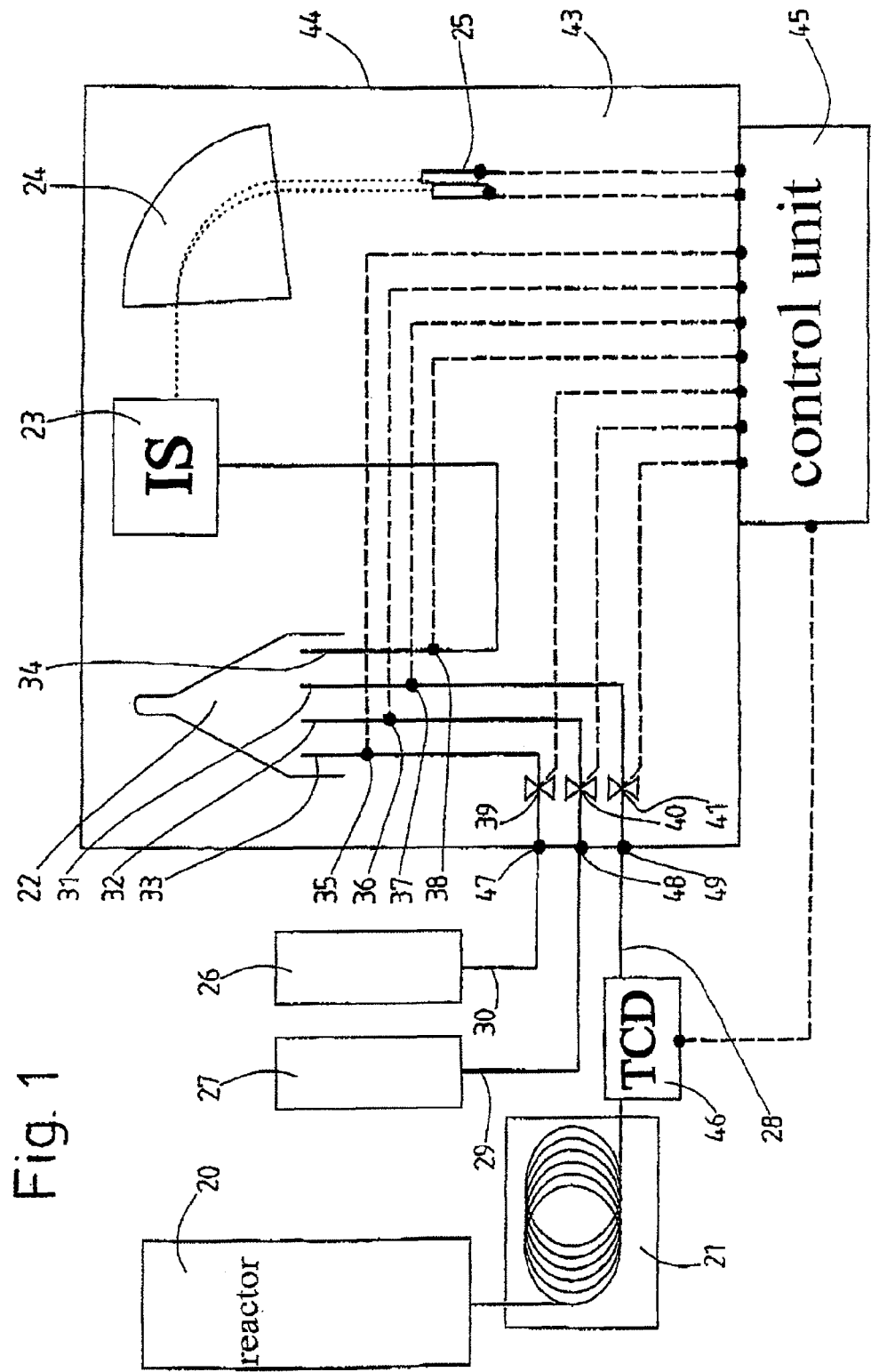
FIG. 1 shows a diagrammatic representation of a device for carrying out the method according to the invention, with reactor, gas chromatograph, open split, ion source, deflection unit, detector and electronic control.

To explain the method according to the invention, reference is first made to FIG. 1. The interaction of the individual components during the isotope ratio analysis of samples which are burnt in a reactor 20 is shown. Gaseous combustion products are conducted through a gas chromatograph 21 and emerge from the latter as sample gases.

The samples gases flow via at least one open split 22 into an ion source 23. The ions formed there pass through a deflection unit 24 to a detector system 25 having preferably several detectors.

The aim of the analysis is an isotope ratio measurement of the sample gases. For this purpose, the sample gases are continuously supplied, alternating with reference gases from a reference gas source 26, to the open split 22. In addition, carrier gas from a carrier gas source 27 can be supplied to the open split 22.

To simplify the pictorial representation, only a sample gas supply 28, carrier gas supply 29 and reference gas supply 30 are drawn in FIG. 1. In fact, several supply lines and sources can be provided in each case.

The individual gases pass into the open split 22 via capillaries, namely sample gas capillary 31, carrier gas capillary 32 and reference gas capillary 33. In addition, a capillary 34 leading to the ion source 23 is provided. This is also called snifting line. Here too, several capillaries can be provided in each case depending on existing supply lines.

The capillaries 31 to 34 can be activated, i.e. moved into the open split and back again by means of known actuators 35 to 38 which are not shown in greater detail. In addition, the capillaries 31 to 34 can be preceded by electronically controllable valves 39 to 42. Because of the risk of fractioning, the capillary 34 (to the analyzer) is operated without a valve, if possible.

Open split 22 with capillaries 31 to 34, actuators 35 to 38 and valves 39 to 42, ion source 23, deflection unit 24 and detector system 25 are here integrated components of an isotope mass spectrometer 43 as analyzer and thus, at the same time, component of one of the same equipment unit which, if possible, is surrounded by a housing 44.

The mass spectrometer 43 is associated with an electronic control, in this case a computer 45 having interfaces for the transmission of data. The computer 45 can be integrated in the mass spectrometer 43 or (as shown in FIG. 1) connected to the mass spectrometer. Electrical lines or data lines and/or control lines, drawn as dashed lines, connect the computer 45 at least to the detector system 25, the actuators 35 to 38 and the controllable valves 39 to 42.

Between the gas chromatograph 21 and the sample gas supply 28, a detector 46 for the concentration of the sample gases is preferably provided, for example for the detection of the thermal conductivity. Correspondingly, the detector 46 is also connected to the computer 45 via a data line.

The various gas supplies 28, 29, 30 can be connected to the mass spectrometer 43 via suitable interfaces, for example couplings 47, 48, 49.

During the measurement of the isotope ratios, the various gas streams are controlled via the computer 45. For this purpose, the valves 39 to 42 are controlled and/or the actuators 35 to 38 are driven for the movement of the capillaries 31 to 34. In addition, the control can be influenced by measurement results, particularly by the analysis results of the detector system 25 and/or the concentration measurement of the detector 46.

Figure 2:
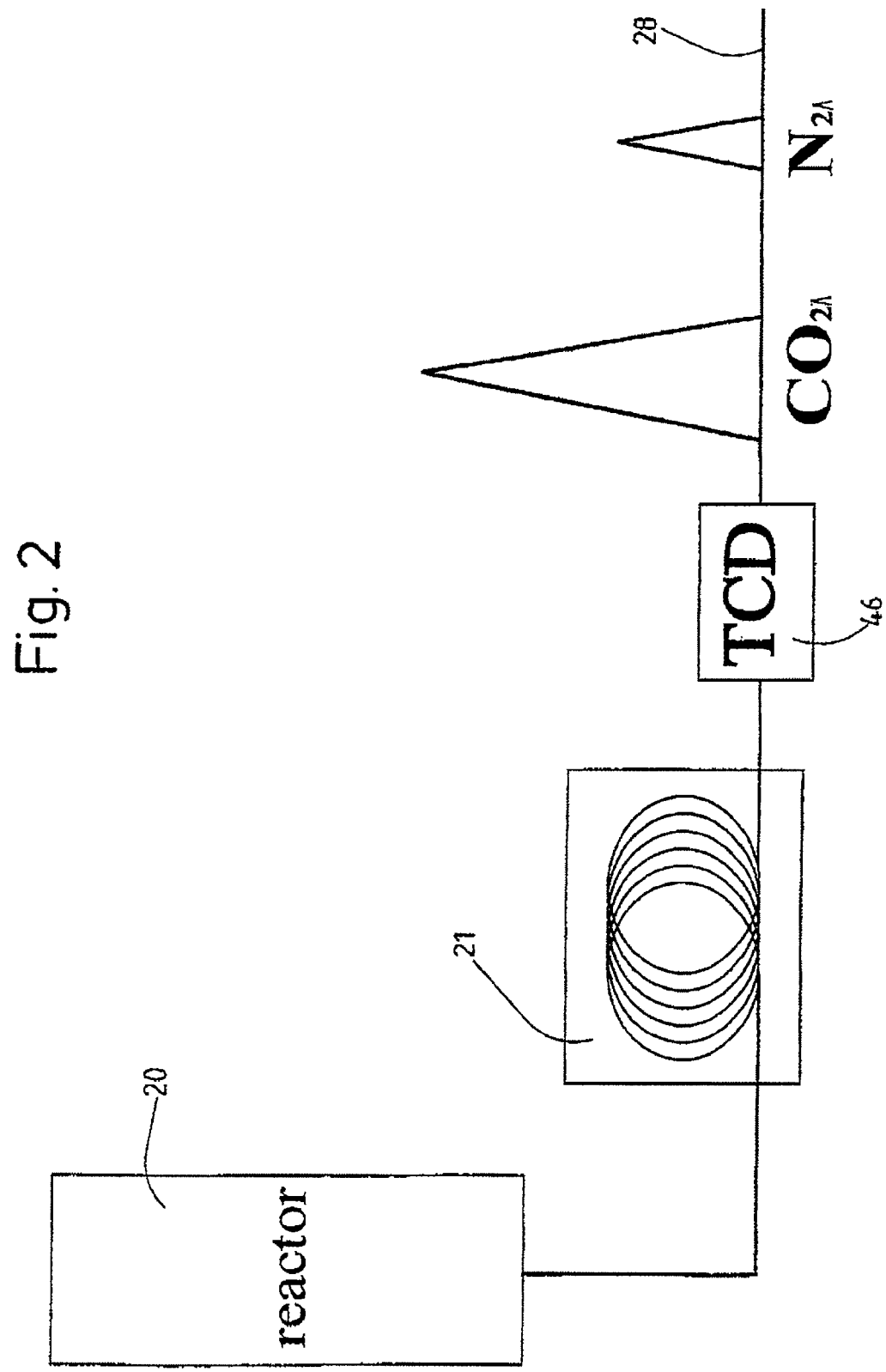
FIG. 2 shows a part of FIG. 1, namely reactor, gas chromatograph and detector for thermal conductivity.

Various examples of measuring sequences will be explained with reference to the further figures:

According to FIG. 2, a substance is converted in the reactor 20, from which, for example, $CO_2$ and $N_2$ are produced. The gases are separated from one another in time in the gas chromatograph 21 and pass via the sample gas supply 28 into the mass spectrometer, not shown.

From the signals of the detector 46, it can be seen that $CO_2$ occurs in significantly greater concentration than $N_2$. This can be taken into consideration by dilution with carrier gas in the area of the open split.

However, the $CO_2$ is the cause of a measuring problem, particularly in conjunction with the determination of isotope ratios. The sample gases are measured alternately with reference gases, as is $CO_2$. This has a chromatographic peak with a long tail so that the $N_2$ determination of the subsequent measurement is disturbed. From $CO_2$, CO is also formed in the ion source of the mass spectrometer which has the same mass-to-charge ratio as $N_2$.

Figure 3:
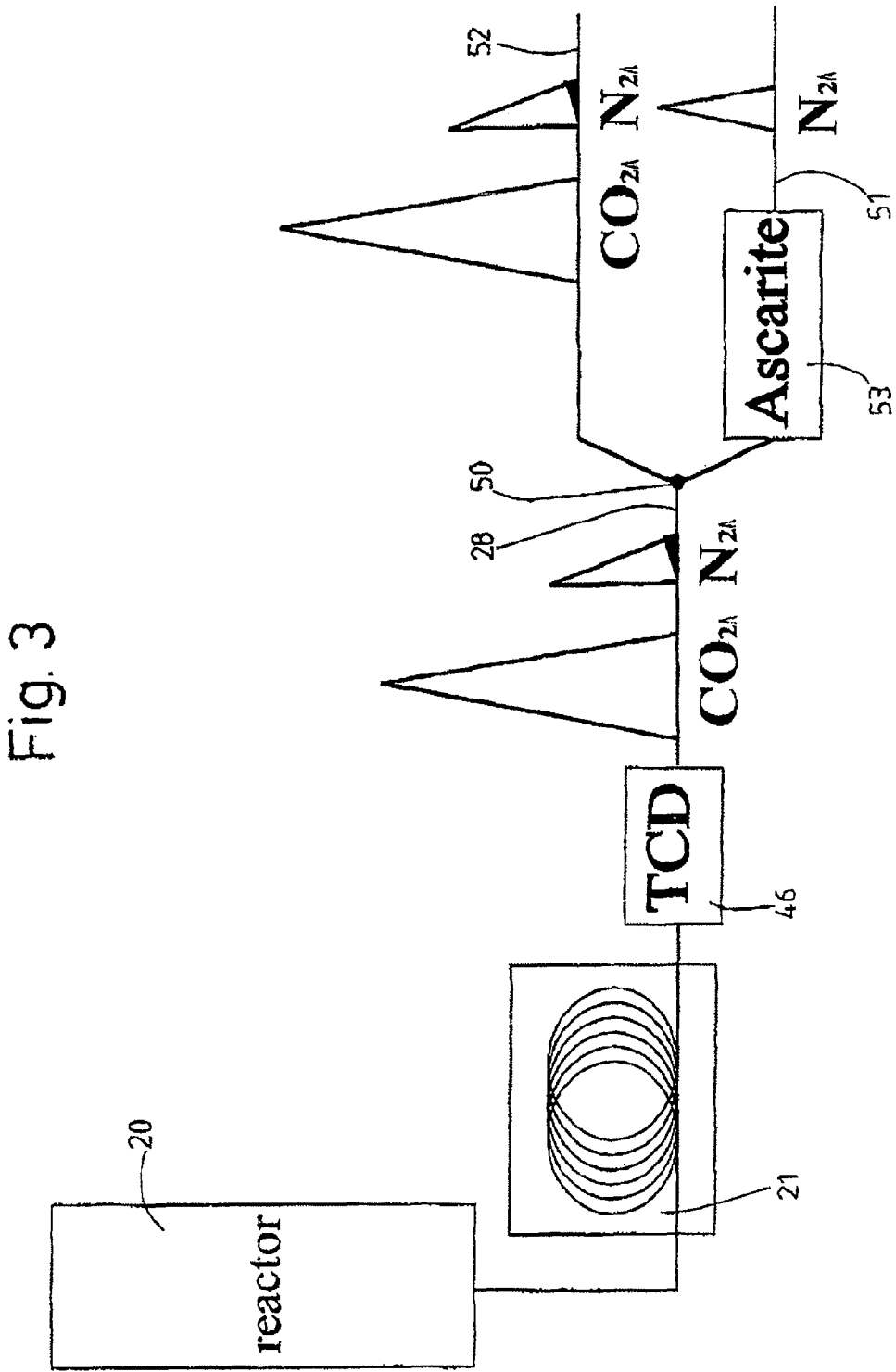
FIG. 3 shows the section according to FIG. 2, but with divider for a sample supply.

To solve the problem described, the sample gas supply 28 is split via a divider 50 to two supply lines 51, 52 as shown in FIG. 3. In the supply line 51, a trap 53 is installed which is here constructed as an ascarite trap in order to hold back the $CO_2$. For this reason, only $N_2$ passes into the open split via the supply line 51 whilst, via line 52, the same gas streams as does through the sample gas supply 28. Naturally, other ways of processing the sample gas stream are also possible.

Figure 4:
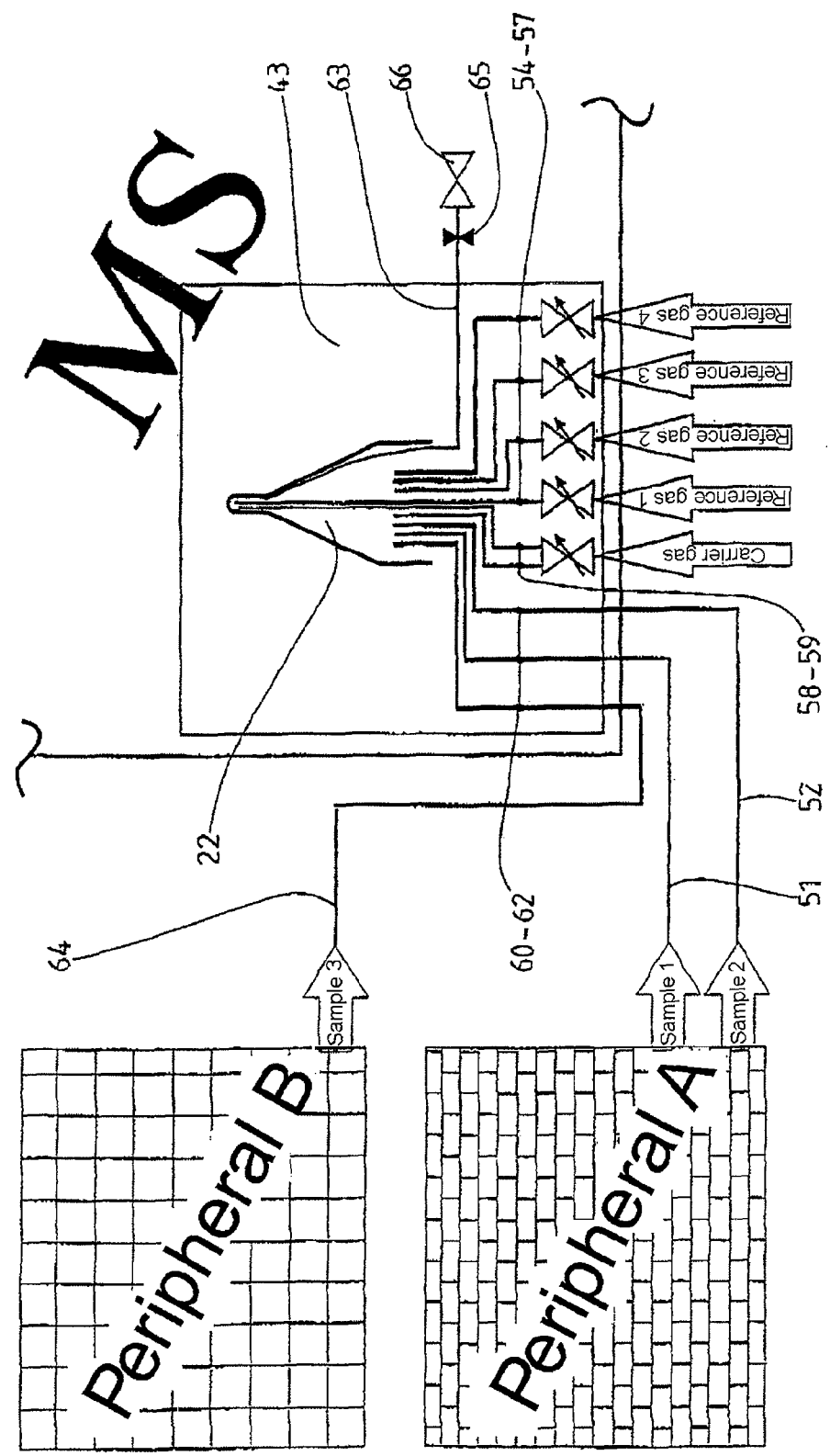
FIG. 4 shows an open split integrated into a mass spectrometer and with two connected peripherals, by means of which a total of three different sample gas streams are generated, the open split having four capillaries for reference gases and two capillaries for carrier gases.

The supply lines 51 and 52 are in each case connected via separate couplings, valves and capillaries to an open split analogously to the representation in FIG. 1 and as shown, for example, in FIG. 4 in the area of a peripheral A. During the measurement of the isotope ratios, $N_2$ and $CO_2$ from the same sample and flowing via the same open split can be measured with the arrangement according to FIG. 3 in the course of a measurement. In this context, a dilution of the gases flowing via the supply line 52 can occur in the area of the open split so that the ideal signal intensity from the point of view of measurements is always present in the mass spectrometer. The concentration is calculated and adapted on the basis of the signals supplied by the detector 46. This type of concentration monitoring and adaptation by dilution can also be carried out with the embodiment according to FIG. 2.

FIG. 4 shows a device according to the invention with the open split 22 as component of the mass spectrometer 43. The open split 22 is here supplied with gases from a multiplicity of capillaries, to which the same number of actuators (not shown) and valves is allocated. For reasons of better clarity, the further components of the mass spectrometer and the computer 45 for the electronic control with the associated data lines are not drawn.

By way of example, four reference gas capillaries 54 to 57, two carrier gas capillaries 58, 59 and three sample gas capillaries 60, 61 and 62 are provided, and a capillary 63 leading to the mass spectrometer. The said reference numbers are also specified in FIGS. 5a to 11d.

The peripheral A is here understood to be a unit for sample processing, for example as shown in FIGS. 1 to 3 and—as can be seen in FIG. 3—with two supply lines 51, 52. Analogously, the peripheral B designates a further unit for sample processing, for instance corresponding to FIGS. 1 and 2, i.e. with only one supply line 64 analogously to the sample gas supply 28.

A special feature is provided in the area of the capillary 63 leading to the ion source, namely a crimped point 65. The capillary 63 is produced of inertized high-grade steel and narrowed to a precisely defined cross section in the area of the crimped point 65. This creates conditions which are reproducible for this capillary. The crimped point 65 is followed by a blocking valve 66 analogously to the valve 42 in FIG. 1.

The open split 22 is structured in accordance with the direct-current principle, see particularly FIG. 5a et seq., namely with capillaries dipping into the open split in parallel with one another from the same direction and correspondingly with sample gases, reference gases and carrier gases flowing into the open split from the same direction.

The open split 22 has a mixing zone 67, a waiting zone 68 and an intermediate transition zone 69. The mixing zone 67 is closed at one end and has a small cross section relative to the waiting zone 68. The ratio of the cross sections to one another is dependent on the space requirement of the capillaries in the area of the waiting zone. The aim is the smallest possible cross section of the mixing zone 67 in order there to be able to achieve the fastest possible gas change for gases alternately supplied.

In the mixing zone 67, at least two different positions are provided, namely an outer mixing position 70 for the capillary 63 leading to the ion source, as their removal position, and an inner mixing position 71 for all remaining capillaries. The terms "inner" and "outer" relate to the distance of the two mixing positions 70, 71 to an inlet area 72 of the open split. The mixing position 70 lying closer to the inlet area 72 is called the outer mixing position since it is nearer than the inner mixing position 71 to the only opening of the open split. The removal position of the capillary 63 can also be provided slightly outside the mixing zone 67 and not at its boundary as here.

The waiting zone 68 also has two waiting positions, namely an outer waiting position 73 for all capillaries with the exception of capillary 63 and an inner waiting position 74 for capillary 63, see for example FIG. 5a.

The transition zone 69 is conically constructed with a very small cross section in the area of the transition to the mixing zone 67 and a very large cross section in the area of the transition to the waiting zone 68. Mixing zone 67 and waiting zone 68 are themselves constructed in each case with cross sections remaining the same over their length. Other embodiments are possible. What is important is that the capillaries can be easily and reproducibly inserted into the mixing zone 67.

In the present exemplary embodiment, the open split 22 is provided with an inlet area 72 pointing downward and is thus particularly suitable for the use of light carrier gases (in comparison with air). The gases accumulate in the area of the mixing zone 67 and displace heavier gases.

In FIG. 5a, only the carrier gas capillary 59 is activated. This means that only this capillary reaches into the mixing zone 67. The carrier gas emerging from the capillary 59 displaces all remaining gases from the mixing zone 67. Gases emerging from the other capillaries do not pass into the capillary 63 since this, in its own waiting position 74, protrudes further into the open split than the remaining unactivated capillaries.

In the representation of FIG. 5b, the carrier gas capillary 59 and the reference gas capillary 4 and the capillary 63 leading to the ion source are activated. Correspondingly, reference gas diluted with carrier gas is conducted into the ion source.

In FIGS. 6a, 6b and 6c, the introduction of one or more carrier gas capillaries into the active volume of the mixing zone 67 is shown. The configuration according to FIG. 6c with two carrier gas capillaries can be combined, for example, with an activated sample gas capillary 60 to 62 (in FIG. 6c, none of the capillaries 60 to 62 is activated) for extreme dilution of very high sample concentrations.

The introduction of carrier gas into the mixing zone 67 is used, for example, for the rapid displacement of highly absorptive gases such as $SO_2$ in order to subsequently be able to carry out experiments with less background. FIG. 6d shows the variation with time of a signal at the detector in the configuration according to one of FIGS. 6a to 6c. Firstly, a strong background signal can be detected, see curve branch 75. After a short time, the underground signal abruptly decreases or is very weak, see curve branch 76.

FIGS. 7a to 7d show the alternating measurement of the signals of a reference gas with a carrier gas (capillaries 57, 59, 63), of a sample with another carrier gas (capillaries 60, 58, 63) and another reference gas with the carrier gas used first (capillaries 59, 56 and 63). In FIG. 7d, the different signal intensities can be recognized, and (the two center) sample signals. The first (larger sample signal) follows the signal for the reference gas of the capillary 57 of almost identical intensity whilst the (weaker) sample signal is followed by the (also weaker) signal for the reference gas from the capillary 56. The different reference gas intensities are adjusted either via different flow rates as properties of the capillaries 56, 57 or via the in each case associated electronic valves which are shown only in FIGS. 1 and 4. Both types of dilution control can also be combined with one another.

FIGS. 8a to 8e show the activation of the various capillaries and the signal intensities in the measurement of two sample streams of a peripheral. In this context, the sample gas capillaries 60, 61 are successively activated. The sample signals are here flanked by reference gas pulses diluted differently with carrier gas, see first and last rectangular signal in FIG. 8e. The sample gas is not diluted in the open split. Correspondingly, FIGS. 8b and 8c do not show any activated carrier gas capillaries. All signals are analyzed within a measuring sequence. This also applies to the other measurements shown.

As previously in FIGS. 8a to 8e, switching takes place between the two sample streams of peripheral A within a measuring sequence in the example of FIGS. 9a to 9e, see center peaks of FIG. 9e. In this case, however, the sample gases are diluted in the open split by carrier gas from the capillary 58. The second sample signal is of lesser intensity. Correspondingly, the intensity of the reference gas from capillary 56 is adapted.

FIGS. 10a to 10e show a measuring sequence with the measurement of two sample streams from the two respective peripherals A and B. Before the two sample signals, the respective reference gases are detected, in the present case the reference gas from capillary 57 diluted with carrier gas from capillary 59 (before the first sample signal) and the reference gas from capillary 56 again diluted with carrier gas from capillary 59. The carrier gases have in each case been added in different quantities in order to adjust the different sample concentrations of the peripheral gases into the range which is optimum for the analyzer. It is thus possible to bring both peripheral signals to about the same intensity.

FIGS. 11a to 11e show three successive sample signals from the same sample capillary 60, but once with constant dilution from an arbitrary capillary (FIG. 11a) and with in each case a different degree of dilution for achieving equal signal intensities at the detector, see FIGS. 11b to 11e. The configuration according to FIG. 11b shows a high degree of dilution via the carrier gas capillary 58. A simple dilution via the carrier gas capillary 59 is shown in FIG. 11c. In the configuration according to FIG. 11d, there is no dilution. The different degrees of dilution result in equally strong signal intensities according to FIG. 11e instead of the different signal intensities according to FIG. 11a which would otherwise have to be expected. For reasons of clarity, the reference gas pulses which are also present are not shown. As also in the other measuring sequences, an automatic gas configuration change of the analyzer takes place after each measurement of sample and reference, for example a change in the magnetic field strength of the deflection unit and changes in the parameters of the ion source.

The computer-controlled or electronically controlled adjustment of concentration of the reference gases and sample gases by increasing or reducing the carrier gas stream has considerable advantages:

Considerably less reference gas is consumed than previously since, as a rule, after a prepressure adjustment, no further control is required and therefore the bleeder capillaries otherwise used are also no longer required for venting pressure reducers. This reduces the operating costs, the maintenance expenditure, the expenditure of reference gas calibration and the hazard potential when using toxic or combustible reference gases.

Accurate sample measurement and knowledge for signal intensity control are no longer mandatorily required since the signal intensity of reference and sample can be automatically adapted to one another by the computer control. Thus, the intensities of the reference gas pulses can be balanced in accordance with the measured sample for achieving an optimum measuring accuracy by controlling the dilution in the open split. In addition, the adjustment of concentration of the sample in the gas can be optimized in near real time if the preceding peripheral contains a preanalysis unit—such as, for example, a flame ionization detector (FID) or a detector for thermal conductivity (TCD)—the result of which allows the sample concentration to be inferred. The sample in the open split can be optimally diluted for achieving the maximum measuring accuracy via the computer control.

Equipment-diagnostics measurements such as a check of linearity or an H3 factor determination to be frequently carried out can also be automated by the computer control. The presence of an experiment is no longer necessary and determinations of the calibration factor can be carried out in association with measurements so that the accuracy of the experiments is again increased.

More complex measuring sequences which assume a variation of the mixing ratio of reference or sample gas in the open split can now be carried out automatically as programmable sequences without having to intervene in the meantime. This additionally increases the utilization of measurements of the device.

The electronic control of the carrier gas or gases in conjunction with the open split shown is particularly advantageous since the latter greatly extends the possibilities of automated measuring sequences.

In a sequence of several identical sample signals, a drift which may occur can be adapted via the automatic dilution adjustment.

Detecting a sample peak before a reference signal is advantageous if the retention time of the sample peak from the peripheral is not precisely known. In this constellation, the intensity of the reference signals to be recorded after the sample peaks can be adjusted optimally in near real time.

A concentration control via the dilution control is free of fractionation.

The device described has the following advantages:

The feed line between open split and analyzer is no longer located outside the latter between the peripheral and the analyzer but rather inside the latter. The capillaries can therefore be protected better against temperature fluctuations and other disturbing influences. The signal stability is improved, which is associated with increased measuring accuracy. This effect is reinforced further by the use of the inertized steel capillary with crimp restriction for the feed line to the analyzer.

When several peripherals are connected, the costs are reduced since only one open split per analyzer is required as interface and not—as previously—one interface per peripheral.

Since now only one open split needs to be flushed with carrier gas, its consumption and the associated costs are reduced.

In comparison with the conventional design of an analyzer, fewer blocking valves are also needed so that the maintenance and cost expenditure is reduced because of the reduced susceptibility to leakage.

A relatively large number of peripherals can be connected simultaneously to the analyzer or to the open split, respectively. The waiting zone 68 offers sufficient space for the increased number of capillaries.

From peripherals, the sample gas stream of which is divided, the different sample gas streams can be supplied as required via different capillaries to the open split and thus to the analyzer.

Switching between the reference gases or the peripherals or different peripheral feed lines, respectively, is greatly simplified since the processes are determined solely by the computer-controlled capillary position in the open split.

The installation of peripherals or the switching between peripherals is possible without air entry into the analyzer and thus with minimum dead times and running-in times.

The automatic switching between the connected reference gases, the peripherals or different peripheral feed lines, respectively, provides for an increased and thus economic utilization of the analyzer operation since automated measuring sequences including different peripherals and peripheral branches are possible without manual intervention.

For applications such as in air analysis, it is advantageous that several reference gases can be supplied to the mass spectrometer at the same time in order to examine and to calibrate interference effects of different isotopes. In addition, a multicomponent mass calibration of the analyzer can be performed when different gases are let in such as, for example, $CO_2$, $SO_2$ and a heavy component such as methyl chloride and others. This allows a mass calibration of the analyzer which is greatly improved, because it is determined over numerous points, and thus a higher measuring accuracy.

In the case of peripherals, the sample preparation of which is associated with a high background and/or even drifts, it is appropriate to also let the background gas of the peripheral into the analyzer during the measurement of the reference gas signal. In conventional technology, this is done via a separate feed line of the open split which is reserved for the sample. In the embodiment according to the invention, this can be implemented by activating carrier gas, sample gas, and reference gas capillaries and capillaries leading to the analyzer. By this means, the reference gas stream can be reduced by more than a factor of 5 which increases the life of a reference gas container by the same factor and reduces the costs associated with the change and the work effort.

When several carrier gas feed lines with different inflows are installed, the concentration of reference and sample gases can be adapted free of fractionation within certain limits to an optimum measuring sequence as part of the measuring routine; see for example FIGS. 11a to 11e.

The waiting position 74 for the capillary 63 leading to the analyzer is located deeper in the open split than the waiting position 73 for the other capillaries so that, in the off configuration, see FIG. 5a, only carrier gas passes into the analyzer and no gas from the other waiting feed capillaries.

The mixing volume kept minimum by the reduced diameter of the mixing zone 67 provides for short switching times and optimum mixing behavior of the gases.

In the case of an open split, the open end of which points downward (as shown in the figures), a carrier gas, the density of which is less than that of the surrounding air, more effectively prevents the breaking-in of air into the interface and the associated disturbance than in the case of an alignment rotated by 180°. The latter is advantageous for the use of carrier gases which have a higher density than air. The device shown by means of the figures would be arranged rotated by 180° in this case.

All lines or capillaries which lead into or out of the open split are continuously flushed with the corresponding operating gases, that is to say also in the wait mode, so that disturbances by contamination such as water, air etc. do not occur in the renewed use and thus the running-in and dead times are greatly reduced.

The device according to the invention, particularly the open split shown, offers numerous possibilities for capillary configurations and switching sequences for the most varied analytical questions. The configuration sequences represented by means of the figures can be arbitrarily combined for a large number of possible applications and are not yet complete, by far.

FIG. 12 shows the principle of the adjustment of a gas stream in a line by mutually parallel valves. As an example, a feed line 80 for a carrier gas helium is here split into eight secondary lines 81 to 88. In each of the secondary lines 81 to 88, a separate valve 89 to 96 is arranged which can be preferably switched electrically between two switching positions, namely open or closed. The valves 89 to 96 are allocated restrictions, not visible in FIG. 12, for example defined cross sectional constrictions of the secondary lines 81 to 88. As a result, the flow rates present in the individual secondary lines differ which, in the present case, are, for example, about 1%/2%/2%/5%/10%/20%/20%/40% of the flow rate of the feed line 80. Opening only single ones of the valves 89 to 96 makes it possible to set almost any values between 1% and 100%. Following the valves 89 to 96, the secondary lines 81 to 88 again lead together to an ongoing line 97 with the resultant flow rate.

In parallel with the secondary lines 81 to 88, a backflush line 98 with its own valve 99 is also provided. Via this line, a pressure reduction in the area of the ongoing line 97 can also be carried out. The latter is, for example, part of a capillary which opens into an open split as will be explained in greater detail by means of FIG. 13 in the text which follows.

Two open splits 100, 101 can be seen as feed devices to a mass spectrometer MS for the gases to be analyzed. The open split 100 is provided for supplying sample gases, the open split 101 for supplying, in this case, five different reference gases. The division into separate sample and reference feed has the advantage that sample streams having a very low flow can also be measured well. The sample streams can be let in either directly or can be mixed with carrier gas in a relatively small mixing zone in the open split 100. The separate supply is also advantageous because of the possibility of measuring the reference simply and reliably "against the background of the sample".

For supplying the reference gases, five feed lines 102 to 106 are provided here via which, for example, $H_2$, $N_2$, $SO_2$, CO and/or $CO_2$ can be supplied to the open split 101 as reference gases. The three feed lines 102 to 104 open into a common capillary 107 which can be moved into the open split 101 or out of it via an actuator. The further feed lines 105, 106 open into a common capillary 108 which can be axially displaced by an actuator in the same manner as the capillary 107.

Figure 13:
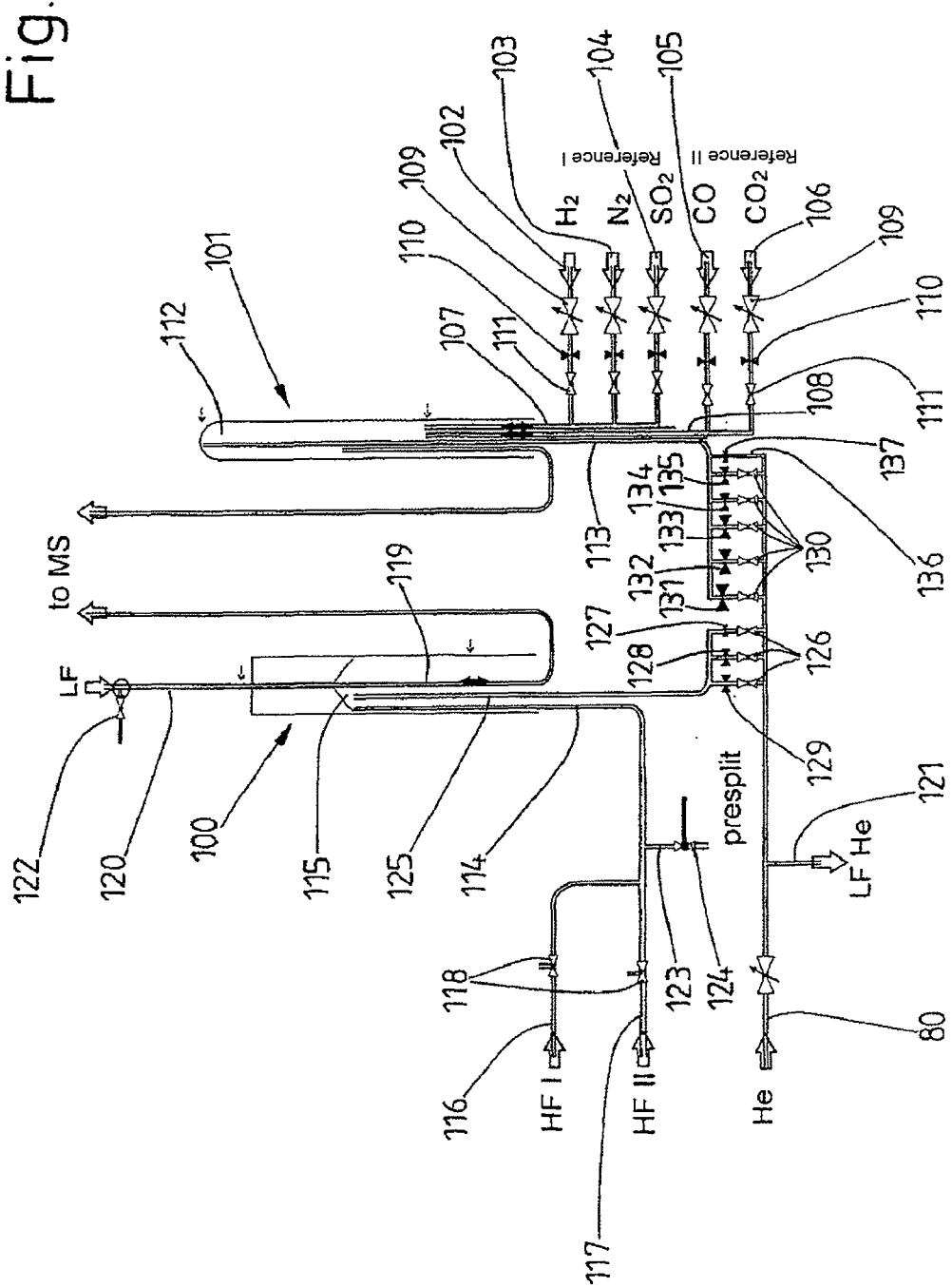
FIG. 13 shows a combination of two open splits for supplying low-flow sample gas, high-flow sample gas, carrier gas (with different gas streams) and reference gas to a mass spectrometer.

Each of the feed lines 102 to 106 is provided with a manual control valve 109, a defined restriction 110 and an electrically switched valve 111. The in each case active reference gas (or reference gases) is preselected via the valves 109 and 111, respectively, and activated into a mixing zone 112 of the open split 101 by moving out the capillaries 107 and 108, respectively. FIG. 13 shows the capillaries 107, 108 in their parked position outside the mixing zone.

Due to the design described, it is possible to keep two or more reference gases in equilibrium and then to supply them alternately, e.g. in the case of the analysis of two or more elements in a sample, possibly after a (gas) chromatography. On the other hand, a large or almost arbitrary number of reference gases can be kept available in automated manner with minimization of the expenditure.

Carrier gas, in the present case helium, enters via a capillary 113 into the open split 101. For this purpose, a valve arrangement according to FIG. 12 is provided. The capillary 113 then has the function of the ongoing line 97 in FIG. 12. According to FIG. 13, the carrier gas supply is arranged in such a manner that a minimum of carrier gas always passes into the open split 101 so that it is always sealed against the environment.

The sample gases are supplied differently depending on the flow rate provided by the peripheral, not shown here. High-flow (HF) samples are conducted via a capillary 114 into a mixing zone 115 of the open split 100. Two feed lines 116, 117 for high-flow samples are shown here. Both feed lines open into the capillary 114 and can be switched via switching valves 118.

Low-flow (LF) samples are introduced into the open split 100 from the opposite side (opposite the capillary 114). A capillary 119 (snifting line) leading from the open split 100 to the mass spectrometer MS can be displaced between two positions, namely between the mixing zone 115 and a capillary 120 for the low-flow sample, by an actuator.

The capillary 119 (snifting line) is matched to the diameter of the capillary 120 and can be dipped into the capillary 120 (as shown FIG. 13). The sample gas stream thus passes virtually completely into the mass spectrometer. This is advantageous in the case of particularly low flow rate of the sample.

If the capillary 119 is not located in the capillary 120 but, instead, is displaced into the mixing zone 50, the sample gas entering in the countercurrent into the open split via the capillary 120 is normally diluted with carrier gas. The latter comes from the feed line 80. However, FIG. 13 shows the capillary 115 dipping into the capillary 120, as mentioned above.

If there is no peripheral for providing low-flow sample gas, carrier gas can be supplied instead via the capillary 120, for example by connecting a branch 121 in the feed line 80 to the capillary 120.

A superfluous low-flow sample can be vented by a venting valve 122 at the capillary 120—e.g. if a high-flow sample is currently being measured.

Depending on the position of the valves 118, the high-flow samples pass into the open split 100 via the capillary 114. The valves 118 are here constructed as three-way valves so that high-flow sample streams not needed in each case can be blocked and vented. As a result, the gas stream remains constant in the preceding peripheral, not shown. This avoids corruption by diffusion.

After the feed lines 116, 117 have been combined to form the capillary 114, the latter has a venting branch 123 which is provided with its own valve 124. The gas stream passing into the capillary 114 can be partially removed via the venting branch 123 by correspondingly switching the valve 124 so that a reduced gas stream passes into the open split 100.

In the mixing zone 115, the sample gas stream is diluted by the carrier gas stream and passes via the capillary 119 into the mass spectrometer. Instead of the mass spectrometer, another suitable detector can also be provided.

The dilution of the sample gas stream is controlled via a control of the carrier gas stream. The carrier gas stream passes via a capillary 125 into the open split 100. Between feed line 80 and capillary 125, several valves 126 are here arranged in parallel with one another, namely three valves 126 with in each case subsequent restrictions 127, 128, 129 which are differently designed. By selecting the individual valves 126 or combinations of these, the most varied carrier gas streams can be set in the capillary 125. A continuous supply from the feed line 80 into the capillary 125 is not required since high-flow peripherals frequently already contain a basic stream or a separate carrier gas. Computer-aided control of the valves 126 ensures that there is always sufficient flow in the open split 100 and thus no environmental gas can flow in.

In the present case, five valves 127 which are parallel to one another and which are also electrically switchable like the valves 123 are arranged between the feed line 80 and the capillary 113. To each valve 127, a defined restriction 131 to 135 is allocated. Furthermore, a line 136 without valve, via which a basic stream of carrier gas always flows into the open split 101, is provided in parallel with the valves 130. The line 136, too, has a defined restriction 137.

The restrictions 131 to 135 (analogous to the restrictions 127 to 129) are arranged to be stepped, for example as shown in FIG. 12, or e.g. in binary steps, namely with flow rates which are to be doubled in each case (single, double, quadruple, eight-fold etc.). The flow rate would then increase by a factor of 2 from one restriction to the next. As an alternative, a greater factor can also be used, e.g. 2.5, so that flow rates 1/2.5/6.25/15.625 etc. are obtained. The higher the factor the fewer valves are needed for a high dynamic range, the step width becoming greater, however. Achieving a desired dilution of the reference gases or sample gases by correspondingly driving the valves 126, 130 is done by a computer-controlled control unit which in each case sets the nearest achievable dilution step.

In order to keep the inflow pressure (peripheral) constant, a certain minimum flow may be necessary. In this case, the absolute minimum supply is provided for this purpose via line 136 with a restriction 137. Instead, it is also possible to provide simply only a secondary condition in the switch control, that at least one of the valves 130 or 126 must be open or additional venting is provided which, if necessary, is only used when all flows in the direction of the target stream are closed.

All restrictions adjoining the feed line 80 are preferably matched to one another. For example, restrictions 129/128/127/131/132/133/134/135 and 137 have flow rates of 7/2/1/35/16/5/2/1 and 2.

The valve 99 already explained by means of FIG. 12 is not shown in FIG. 13 but can also be provided and is also used for venting if a particularly rapid control characteristic is desired and a fast reduction of the pressure is to be achieved or when the ongoing line 97 is connected to a system which is closed earlier and which builds up a counterpressure.

The said restrictions 110, 127 to 129 and 131 to 137 can be implemented in various manners, for example by similar capillaries of different length, by different openings in a flow diaphragm, by defined cross sections etc.

The control of the gas stream for the carrier gas as described is particularly advantageous once a particular constellation of the valves 126 or 130 or 89 to 96 is set and there is no further control via feedback. The desired flow rate is available virtually immediately. The measurements are not disturbed by correcting processes. As well, there are smaller dead volumes than in conventional flow controllers. It can be easily built up from simple known components and also from inert materials. Using the flow controller designed to be binary or incremental due to the valves 89 to 96, 126 and 130 is particularly advantageous especially in conjunction with open splits since, in this case, both the primary pressure (due to a usually mechanical pressure controller at the carrier gas supply) and the target pressure (due to the exposition of the open split to the environment/atmosphere) are constant.

The binary or incremental flow control via the mutually parallel valves as described is possible in conjunction with various devices and methods, that is to say not only for diluting the samples and references in isotope mass spectrometry but, e.g., also in the carrier gas control for ICP-MS, in collision-gas control of collision and reaction cells etc.

The venting valve 122 and/or the valve 124 in the venting branch 123 could also be switched under computer control and operated aligned with the remaining parts explained by means of FIG. 13.

LIST OF REFERENCE DESIGNATIONS

20 Reactor
21 Gas chromatograph
22 Open split
23 Ion source
24 Deflection unit
25 Detector system
26 Reference gas source
27 Carrier gas source
28 Sample gas supply
29 Carrier gas supply
30 Reference gas supply
31 Sample gas capillary
32 Carrier gas capillary
33 Reference gas capillary
34 Capillary to the ion source
35 Actuator
36 Actuator
37 Actuator
38 Actuator
39 Valve
40 Valve
41 Valve 42 Valve
43 Isotope mass spectrometer
44 Housing
45 Computer for electrical control
46 Detector
47 Coupling
48 Coupling
49 Coupling
50 Divider
51 Supply line
52 Supply line
53 Trap
54 Reference gas capillary
55 Reference gas capillary
56 Reference gas capillary
57 Reference gas capillary
58 Carrier gas capillary
59 Carrier gas capillary
60 Sample gas capillary
61 Sample gas capillary
62 Sample gas capillary
63 Capillary leading to the ion source
64 Supply line
65 Crimped point
66 Blocking valve
67 Mixing zone
68 Waiting zone
69 Transition zone
70 Outer mixing position
71 Inner mixing position
72 Inlet area
73 Outer waiting position
74 Inner waiting position
75 Curve branch
76 Curve branch
80 Feed line
81 Secondary line
82 Secondary line
83 Secondary line
84 Secondary line
85 Secondary line
86 Secondary line
87 Secondary line
88 Secondary line
89 Valve
90 Valve
91 Valve
92 Valve
93 Valve
94 Valve
95 Valve
96 Valve
97 Ongoing line
98 Backflush line
99 Valve
100 Open split
101 Open split
102 Feed line
103 Feed line
104 Feed line
105 Feed line
106 Feed line
107 Capillary
108 Capillary
109 Manual control valve
110 Restriction
111 Electrical valve
112 Mixing zone
113 Capillary
114 Capillary
115 Mixing zone
116 Feed lines
117 Feed lines
118 Switching valves
119 Capillary (snifting line)
120 Capillary (low-flow)
121 Branch
122 Venting valve
123 Venting branch
124 Valve
125 Capillary
126 Valves
127 Restriction
128 Restriction
129 Restriction
130 Valve
131 Restriction
132 Restriction
133 Restriction
134 Restriction
135 Restriction
136 Line
137 Restriction

What is claimed is:

1. A device for supplying gases to at least one analytical device, comprising:
an open split (22) which has a mixing zone (67) and a waiting zone (68), and
capillaries (31-33, 54-62) for sample gas and carrier gas and a capillary (34) for removing the gases and for supplying the gases to the analytical device,
wherein the capillaries can be moved from the waiting zone into the mixing zone (67) or to the mixing zone and back again,
wherein at least two of the capillaries are provided for sample gases, and
wherein the movable capillaries each have their own drive for the movement between the mixing zone and the waiting zone.

2. The device as claimed in claim 1, wherein the drives for the capillaries are actuators (35-38).

3. The device as claimed in claim 1, wherein the drives for the capillaries (31-34, 54-63) are driven by a common central control unit.

4. The device as claimed in claim 1, wherein the waiting zone (68) has a larger cross section than the mixing zone (67).

5. The device as claimed in claim 1, wherein the length of the mixing zone in the direction of the capillaries is greater than the width of the mixing zone (67).

6. The device as claimed in claim 1, wherein the capillary (34, 63) for removing the gases is connected to a line which consists of inertized high-grade steel.

7. The device as claimed in claim 1, wherein the open split (22) is arranged inside an isotope mass spectrometer (43).

8. The device as claimed in claim 1, wherein capillaries (31-33, 54-62) with different effective flow rates are provided at least for one of the gases—sample gas, carrier gas, reference gas.

9. The device as claimed in claim 1, wherein capillaries (31-33, 54-62) with different cross sections are provided at least for one of the sample gas and the carrier gas.

10. A device for supplying gases to an analytical device, wherein a particular gas stream can be adjusted in a gas line, with a feed line (80) and at least one ongoing line (97) and several valves (89 to 96) between the feed line (80) and the ongoing line (97),
wherein the valves (89 to 96) are connected in parallel with one another and can be switched step by step in a binary or incremental manner, and
wherein an incoming gas stream is diluted.

11. The device as claimed in claim 10, wherein a defined restriction having a corresponding flow rate is allocated to each valve (89 to 96).

12. The device as claimed in claim 11, wherein the restrictions of at least two of the valves are different.

13. The device as claimed in claim 12, wherein the restrictions of at least two of the valves differ from one another, and the flow rates of the differing valves differ by the same factor.

14. The device as claimed in claim 10, wherein the valves (89 to 96) are controlled manually, electrically or electronically.

15. The device as claimed in claim 10, wherein a parallel line (136) without valve is additionally provided for the connection of feed line (80) and ongoing line (97).

16. The device as claimed in claim 10, further comprising an open split, (101), following the ongoing line (97 or 113, respectively), for mixing the gas stream with another gas stream.

17. The device as claimed in claim 10, further comprising a mass spectrometer following the open split or the open splits (100, 101) as analyzer.

18. The device as claimed in claim 16, wherein the open split or one of the open splits (100, 101) has a first capillary (114) for supplying gas with a high flow rate and a second capillary (120) for supplying gas with a comparatively low flow rate.

19. The device as claimed in claim 18, wherein the open split (100) has a snifting capillary (119) for removing gas which is arranged in the direct current relative to the first or second capillary (114, 120) and which is arranged in the countercurrent to the respective other capillary (120, 114).

20. The device as claimed in claim 19, wherein the second capillary (120) for supplying gas with a low flow rate is arranged in the countercurrent to the snifting capillary (119).

21. The device as claimed in claim 20, wherein the snifting capillary (119) has an outside diameter which is smaller than the inside diameter of the second capillary (120) for supplying gas with a low flow rate and in that snifting capillary and second capillary are arranged movably relative to one another and coaxially, in such a manner that in one position of the two capillaries, these dip into one another.

22. The device as claimed in claim 16, wherein the open split or one of the open splits (100, 101) has a capillary (114) for supplying gas and in that the capillary has a branch (123) which can be closed via a valve (124).

23. The device as claimed in claim 16, wherein the open split or one of the open splits (100, 101) has a capillary (114) for supplying gas and in that two or more feed lines (116, 117) open into this capillary.

24. The device as claimed in claim 23, wherein the feed lines (116, 117) have multi-path valves (118) which let the gas pass in the direction of the open split (100) in one switch position and divert the gas in another switch position.

25. The device as claimed in claim 10, wherein carrier gas is supplied into two different open splits (100, 101) via the feed line (80), in that sample gas can be supplied into one of the open splits via a capillary, in that reference gas can be supplied into the other open split via a capillary, and in that, from both open splits, snifting capillaries lead to an analytical device.

26. The device as claimed in claim 1, wherein the open split (22) which has the mixing zone (67) and the waiting zone (68), and further comprising a capillary for reference gas.

27. The device as claimed in claim 1, wherein the at least two capillaries for sample gas are movable and in each case have their own drive for the movement between mixing zone (67) and waiting zone (68).

28. The device as claimed in claim 1, further comprising an analytical device for isotope ratio analysis.

29. The device as claimed in claim 10, further comprising an analytical device for isotope ratio analysis.

30. The device as claimed in claim 1, wherein configured for dilution of an incoming gas stream.

* * * * *